United States Patent [19]
Comoglio et al.

[11] Patent Number: 5,594,105
[45] Date of Patent: Jan. 14, 1997

[54] PEPTIDE INHIBITORS OF MITOGENESIS AND MOTOGENESIS

[75] Inventors: Paolo Comoglio, Turin; Carola Ponzetto, Moncalieri, both of Italy

[73] Assignee: Farmitalia Carlo Erba S.r.l., Milan, Italy

[21] Appl. No.: 266,514

[22] Filed: Jun. 27, 1994

[30] Foreign Application Priority Data

Jun. 30, 1993 [GB] United Kingdom ............ 9313528
Apr. 18, 1994 [GB] United Kingdom ............ 9407673

[51] Int. Cl.$^6$ .................. A61K 38/10; C07K 7/00
[52] U.S. Cl. .................. 530/326; 530/300; 530/324; 530/327; 530/328; 530/334
[58] Field of Search .................. 530/300, 324, 530/326, 327, 328, 334; 514/12, 13, 14, 15, 2

[56] References Cited

PUBLICATIONS

Molecular and Cellular Biology, vol. 13, No. 3, Mar. 1993, S. Felder, et al., "SH2 Domains Exhibit High-Affinity Binding to Tyrosine-Phosphorylated Peptides Yet Also Exhibit Rapid Dissociation And Exchange", pp. 1449–1455.
Nature, vol. 369, No. 6480, Jun. 9, 1994, Luc. E. M. Marengere, et al., "SH2 Domains Specificity And Activity Modified By A Single Residue", pp. 502–505.
Cell, vol. 77, No. 2, Apr. 1994, pp. 261–271, C. Ponzetto, et al., "A Multifunctional Docking Site Mediates Signaling and Transformation By The Hepatocyte Growth Factor/Scatter Factor Receptor Family".
Molecular and Cellular Biology, vol. 13, No. 8, Aug. 1993, pp. 4600–4608, C. Ponzetto, et al., "A Novel Recognition Motif For Phosphatidylinositol 3-Kinase Binding Mediates Its Association With The Hepatocyte Growth Factor/Scatter Factor Receptor".
Songyang et al, "SH2 Domains Recognize Specific Phosphopeptide Sequences", Cell, vol. 72, pp. 767–778 (Mar. 12, 1993).
Fantl et al, "Distinct Phosphotyrosines On A Growth Factor Receptor Bind To Specific Molecules That Mediate Different Signaling Pathways", Cell, vol. 69, Pates 413–423 (May 1, 1992).
Sawyers et al, "Chronic Myelomonocytic Leukemia: Tel-A-Kinase What Ets All About", Cell, vol. 77, pp. 171–173 (Apr. 22, 1994).

*Primary Examiner*—Christine M. Nucker
*Assistant Examiner*—Benet Prickril
*Attorney, Agent, or Firm*—Oblon, Spivak, McClelland, Maier & Neustadt, P.C.

[57] ABSTRACT

The invention in the field of cell biology relates to novel peptides able to interact with intracellular signal transducers, thus interfering with signal transduction pathways leading to cell proliferation and motility. The peptides of the invention may be chemically synthesized from single amino acids and/or preformed peptides of two or more amino acid residues.

The peptides of the invention find an useful application in the treatment of a neoplastic disease.

17 Claims, 18 Drawing Sheets

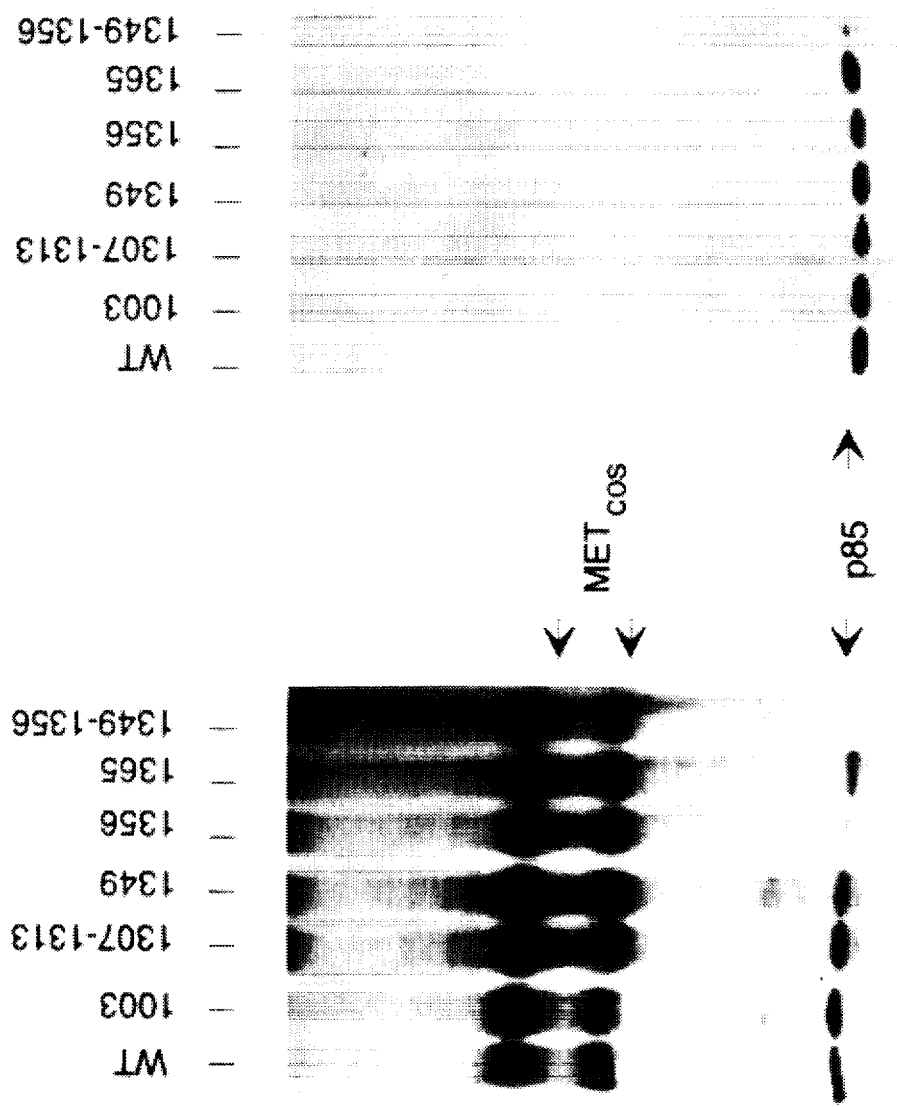

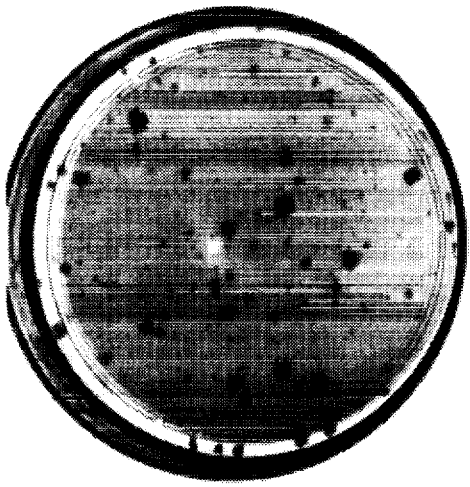
FIG. 8B — TPR-MET Phe^1349
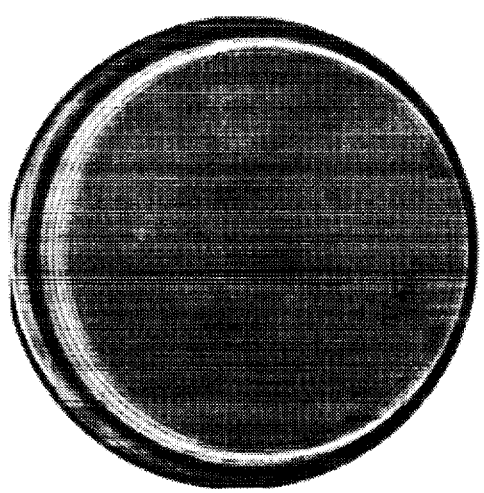
FIG. 8D — TPR-MET Phe^1349-1356
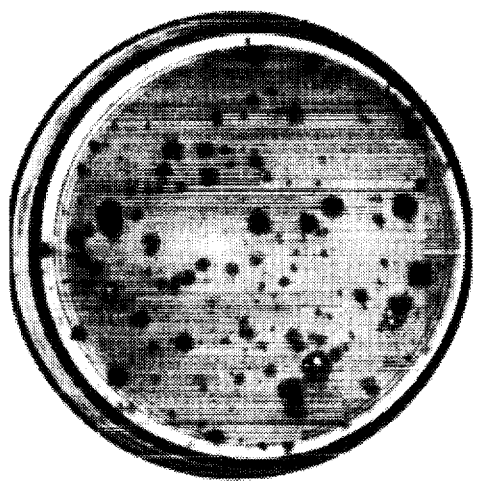
FIG. 8A — TPR-MET
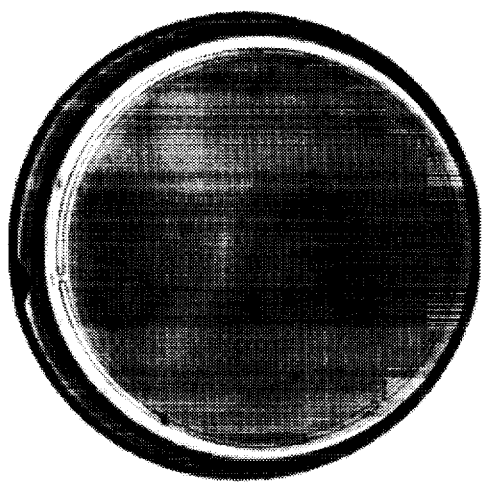
FIG. 8C — TPR-MET Phe^1356

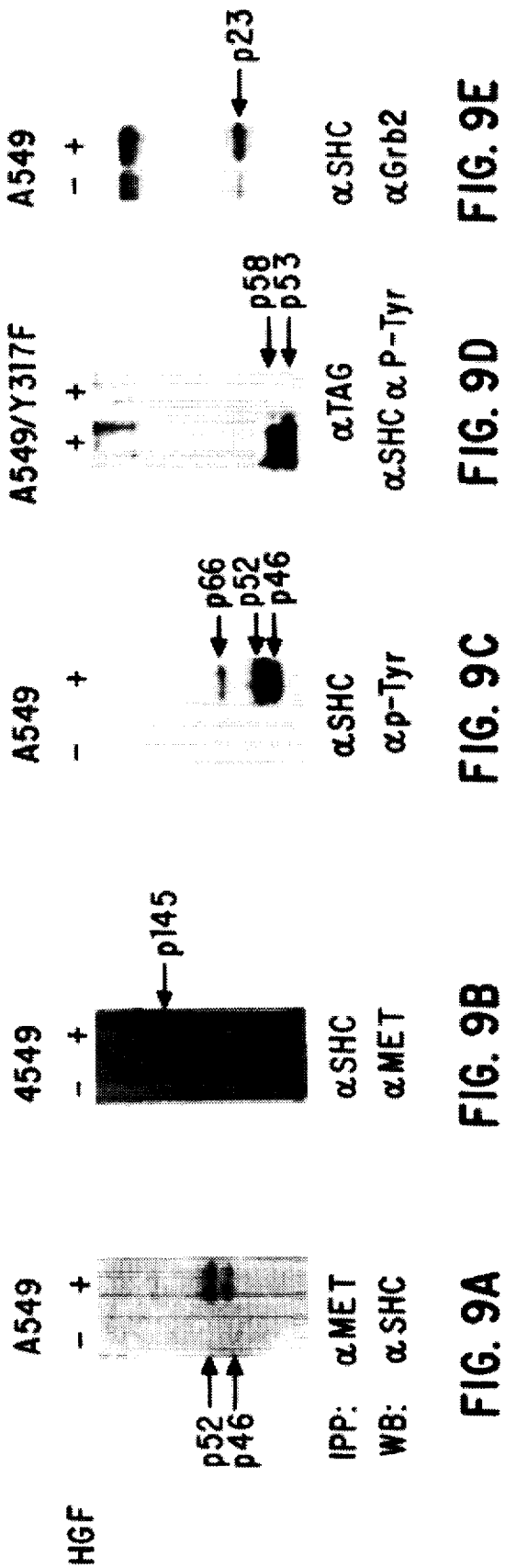

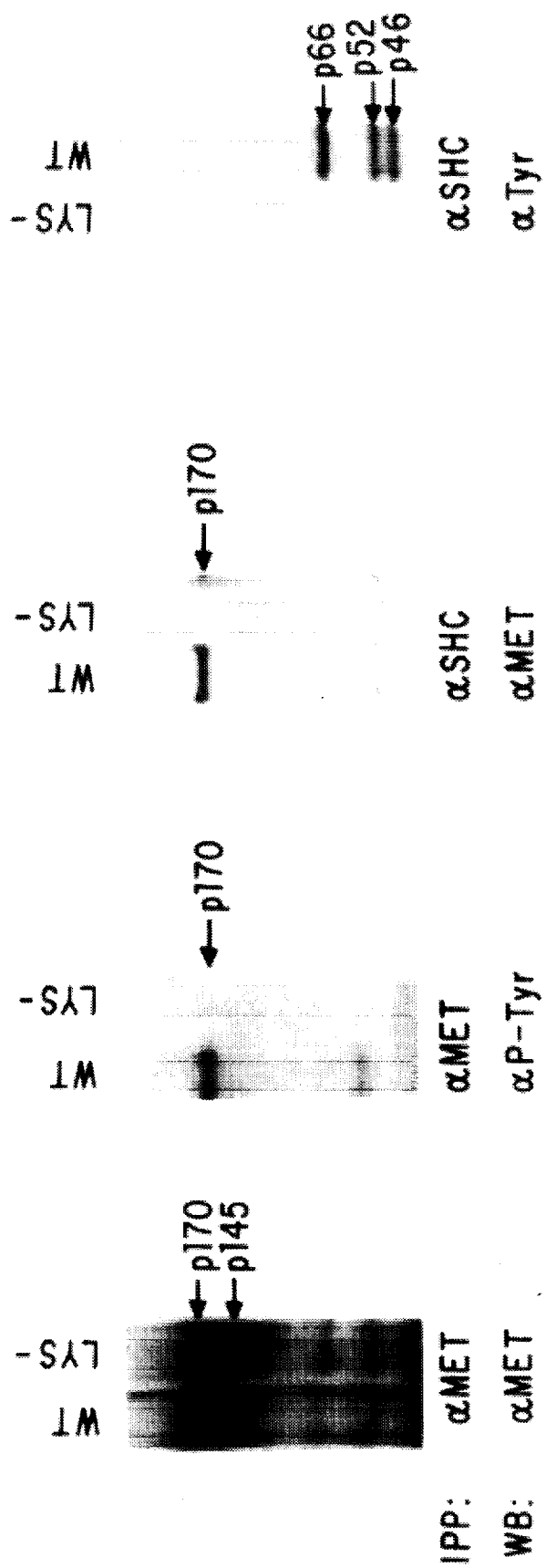

PEPTIDE INHIBITORS OF MITOGENESIS AND MOTOGENESIS

FIELD OF THE INVENTION

The invention in the field of cell biology relates to novel peptides able to interact with intracellular signal transducers, thus interfering with signal transduction pathways leading to cell proliferation and motility.

DESCRIPTION OF THE BACKGROUND ART

Polypeptide growth factors mediate their physiological responses by binding cell surface receptors with tyrosine kinase enzymatic activity (reviewed in Ullrich, A. and Schlessinger, J., Cell 61: 203–211 (1990)).

Upon binding of these ligands, growth factor receptors undergo dimerization followed by the autophosphorylation of specific tyrosine residues.

Among the intracellular milieu of proteins are molecules with defined biological functions that serve as substrates for ligand-activated tyrosine kinase receptors.

The experimental evidences accumulated in the last few years indicate that, upon binding to the receptor, these substrate molecules switch into an activated form and become part of the critical signaling pathway used by growth factors to control cell proliferation.

A number of the cytoplasmic molecules that mediate cellular response to growth factors have been shown to interact with activated receptors through their SRC homology region 2 (SH2) domain (Koch, C. A., et al., Science 252: 668–674 (1991)).

The SH2 domain is a conserved protein module of approximately 100 aminoacids which is found in a remarkably diverse group of cytoplasmic signaling proteins.

Proteins with SH2 domains frequently possess another distinct sequence of about 50 residues, the SH3 domain, which is also implicated in the regulation of protein-protein interactions during signal transduction (see Clark, S. G., et al., Nature 356: 340–344 (1992) and references therein).

Receptor autophosphorylation following ligand binding acts as a molecular switch to create binding sites for the SH2 domain of the cytoplasmic signaling proteins (Anderson, D., et al., Science 250: 979–982 (1990)), which thereby become targets for activation.

SH2 domains directly recognize phosphotyrosine (Matsuda, M., et al., Science 248: 1537–1539 (1990)).

However, high affinity binding of an SH2 domain requires that the phosphotyrosine be embedded within a specific amino acid sequence, as originally suggested by an examination of SH2-binding sites (Cantley, L. C., et al., Cell 64: 281–302 (1991)).

For example, the SH2-containing proteins phosphatidylinositol (PI) 3-kinase, the Ras GTP-ase-activating protein (Ras GAP) and phospholipase C-γ (PLC-γ) each bind to different autophosphorylation sites of the β receptor for platelet-derived growth factor (Kashishian, A., et al., EMBO J. 11: 1373–1382 (1992); Fantl, W. J., et al., Cell 69: 413–423 (1992)).

Autophosphorylation sites acting as specific docking sites for PI 3-kinase, PLC-γ and Ras GAP, have been identified also in epidermal growth factor receptor (EGF-R), colony-stimulating factor 1 receptor (CSF-1R) and fibroblast growth factor receptor (FGF-R) (Cantley, L. C., et al., Cell 64: 281–302 (1991); Mohammadi, M., et al., Mol. Cell. Biol. 11: 5068–5078 (1991); Reedijk, M., et al., EMBO J. 41: 1365–1372 (1992); Rotin, D., et al., EMBO J. 11: 559–567 (1992)).

It has been demonstrated that relatively short peptide sequences corresponding to PDGF receptor phosphorylation sites inhibited the interaction between the activated PDGF receptor and PI 3-kinase (Escobedo, J. A., et al., Mol. Cell. Biol. 11: 1125–1132).

The residues immediately C-terminal to the phosphotyrosine, especially those at the +1, +2 and +3 positions, appear to provide selectivity for specific SH2 domains.

Thus, a recognition motif for the p85 submit of PI 3-kinase has been identified in the PDGF receptor: the sequence is Tyr-Met/Val-Xxx-Met (YMXM or YVXM) (SEQ. ID NOS: 1 and 2) wherein Xxx and X represent any amino acid residue in the three-letter or one-letter code respectively (Domchek, S. M., et al., Biochemistry 31: 9865–9870 (1992)).

The identification of new members of the SH2-containing molecules family as well as of the respective recognition motif is rapidly proceeding.

A direct involvement of some of these molecules in eliciting the biological response to a ligand has been demonstrated. This is the case for the protein Grb2 which associates, through its SH2 domain, to both EGF receptor upon ligand stimulation.

Microinjection of Grb2 and H-ras protein into mammalian cells resulted in the stimulation of DNA synthesis and hence in a mitogenic effect (Lowenstein E. J., et al., Cell 70: 431–442 (1992)).

These results indicate that Grb2 plays a crucial role in the mechanism for growth factor control of ras signaling.

While most of the efforts in the last few years have been concentrated on the study of the interaction between cytoplasmic signaling proteins and the best characterized EGF and PDGF receptors, the authors of the present invention have focused their attention on the hepatocyte growth factor (HGF) receptor.

HGF, also known as Scatter Factor (SF), is a heterodimeric protein secreted by cells of mesodermal origin (Stoker, M., et al., Nature 327: 239–242 (1987); Weidner, K. M., et al., J. Cell Biol. 111: 2097–2108 (1990)).

The factor induces a spectrum of biological activities in epithelial cells, including mitogenesis, stimulation of cell motility and promotion of matrix invasion (Nakamura, T., et al., Biochem. Biophys. Res. Comm. 122: 1450–1459 (1984); Stoker, M. et al., Nature 327: 239–242 (1987); Weidner, K. M., et al., J. Cell. Biol. 111: 2097–2108 (1990); Rubin, J. S. et al., Proc. Natl. Acad. Sci. U.S.A. 88: 415–419 (1991)).

HGF/SF is also a morphogen in vitro (Stern C. D. et al., Development 110: 1271–1284 (1990); Montesano et al. Cell 66: 697–711 (1991)) and a potent angiogenic factor in vitro and in vivo (Bussolino, M. F., et al., J. Cell Biol. 119: 629–641 (1992)).

While the biological effect of HGF/SF varies depending on the target cell, the HGF/SF signal is mediated by a single receptor, the tyrosine kinase encoded by the MET protooncogene (for a review see Comoglio, P. M. in I. D. Goldberg and E. M. Rosen (eds), Hepatocyte Growth Factor—Scatter Factor (HGF/SF) and the C-Met Receptor, Birkhauser Verlag Basel/Switzerland).

The HGF receptor, also known as $p190^{MET}$, is a heterodimeric receptor made of an extracellular α and a transmembrane β subunit (Giordano, S., et al., Nature 339:

155–156 (1989)), both originating from proteolytic cleavage of a common single chain precursor of 170 kDa (Giordano, S., et al., Oncogene 4: 1383–1388 (1989)).

NIH3T3 fibroblasts transfected with the human MET cDNA express functional receptors and respond to HGF/SF with increased motility and invasion of extracellular matrices (Giordano S. et al. PNAS, 90: 649–653 (1993)).

Uncontrolled tyrosine kinase activity of the HGF/SF receptor has been observed in transformed cell lines, following chromosomal rearrangements (Park et al., Cell 45: 895–904 (1986)), gene overexpression (Giordano S. et al., Nature 339: 155–186 (1989)), defective post-translational processing (Mondino et al., Mol. Cell. Biol. 11: 6084–6092 (1991)) and autocrine loop.

Overexpression of the receptor has been observed in a number of human tumors of epithelial origin (Di Renzo et al., Oncogene 6: 1997–2003 (1991); Di Renzo et al., Oncogene 7: 2549–2553 (1992); Prat et al., Int. J. Cancer 49: 323–328 (1991)).

This emphasizes the oncogenic potential of the HGF/SF receptor.

Little is known about the signal transduction pathways triggered by HGF/SF.

The pleiotropic biological response induced by the factor suggests that more than one mechanism may be activated.

The present inventors have previously shown that the HGF/SF receptor associates in vitro, upon autophosphorylation, PI 3-kinase, ras-GAP, PLC-γ and Src-related tyrosine kinases (Bardelli, A., et al., Oncogene 7: 1973–1978 (1992)).

Association of PI 3-kinase with the activated receptor has also been found in vivo, in cells stimulated by HGF/SF (Graziani, A., et al., J. Biol. Chem. 266: 22087–22090 (1991)).

Recently, the authors have also shown that HGF/SF activates Ras by increasing the turnover between its GDP- and GTP-bound state through the stimulation of a guanine nucleotide exchange factor (Graziani, A., et al., J. Biol. Chem. in press (1993)).

We have now found that the HGF/SF receptor associates with the proteins Shc and Gbr2. The mammalian gene Shc encodes three widely expressed overlapping proteins of 66, 46 and 52 kDa (p66$^{Shc}$, p46$^{Shc}$ and p52$^{Shc}$) containing a C-terminal SH2 domain and a N-terminal collagen-homology region (Pelicci et al, Cell 70: 93–104 (1992)). p46$^{Shc}$ and p52$^{Shc}$ are encoded by the same transcript by employing two different ATGs.

p66$^{Shc}$ is encoded by an alterantively spliced transcript (Migliaccio et al, in preparation). Experimental evidence indicates that Shc proteins are implicated in the transduction of signals generated by tyrosine kinase receptors. Among these, Shc proteins are rapidly tyrosine-phosphorilated in response to activation of the EGF (Pelicci et al, ibid) and PDGF (unpublished data) receptors, Erb-B-2 (Segatto et al., Oncogene 2105–2112 (1993)), Src and Fps (McGlade et al, Proc. Natl. Acad. Sci. USA 89: 8869–8873 (1992)). Overexpression of Shc proteins induces neurite outgrowth in PC12 pheochromocytoma cells, and this effect is blocked by the expression of a dominant-negative Ras mutant (Rozakis-Adcock et al., Nature 360: 689–692 (1992)). Upon cell stimulation by certain growth factors, Shc proteins form stable complexes with the Grb2/Sem5 adaptor (Lowenstein et al., Cell 70: 431–442 (1992); Rozakis-Adcock et al., ibid). The latter adaptor is known to activate Ras functions by recruiting SoS, a guanine nucleotide exchanger factor (Li et al., Nature 363: 85–87 (1993); Gale et al., Nature 363: 88–92 (1993); Rozakis-Adcock et al., Nature 363: 83–85 (1993); Egan et al., Nature 363: 45–51 (1993); Simon et al., Cell 73: 169–177 (1993); Oliver et al., Cell 73: 179–191 (1993)) to the membrane.

From the above it clearly appears that the interaction between an activated tyrosine kinase receptor and a cytosolic transducer molecule is a critical step in the signaling pathway leading to cell proliferation and motility.

Since these biological responses constitute the most peculiar characteristics of tumor growth and spreading, need for interfering in such interaction is recognized in the art.

SUMMARY OF THE INVENTION

The present inventors have synthesized a group of phosphopeptides able to interact with intracellular signal transducers thus interfering in the pathways leading to cell proliferation and movement and extracellular matrix invasion.

These biological properties can be exploited to inhibit growth of neoplastic cells and to prevent metastatic spreading.

The present inventors have also made the following new findings: (1) Shc proteins bind the tyrosine phosphorylated SF/HGF receptor via the SH2 domain; (2) Shc proteins bind to phosphotyrosine $Y^{1349}$ and $Y^{1356}$ of the SF/HGF receptor tail; (3) overexpression of Shc proteins increases the motogenic response to SF/HGF; (4) Shc proteins are phosphorylated on $Y^{317}$ after binding to the SF/HGF receptor; (5) Shc proteins phosphorylated on $Y^{317}$ form specific complexes with the Grb2 protein; and (6) the Grb2 docking site on Shc ($Y^{317}$VNV) (SEQ. ID NO: 3) has the same sequence as signal transducer binding sites on the HGF/SF receptor (YVNV) (SEQ. ID NO: 3). Thus, we have synthesized peptides from the Grb2 docking site on Shc and from the Shc docking sites containing the recognition motifs $Y^{1349}$VHV (SEQ. ID NO: 4) and $Y^{1356}$VNV (SEQ. ID NO: 3) on the hepatocyte growth factor receptor. These peptides are capable of interfering in the pathways leading to cell proliferation and movement and extracellular matrix invansion.

Accordingly, the present invention further provides a peptide having the sequence of a portion of Shc protein, which peptide can bind to a cytosolic signal transducer. The peptide is generally capable of inhibiting binding between Shc protein and Grb2 protein or between Grb2 and the activated hepatocyte growth factor receptor.

Moreover, the present invention provides a peptide having the sequence of a portion of the intracellular region of the human hepatocyte growth faction receptor, which peptide can bind to a cytosolic signal transducer.

The peptide is generally capable of inhibiting binding between Shc protein or the p85 subunit of phosphatidyl inositol 3-kinase and the activated hepatocyte growth factor receptor or between Shc and other cytosolic signal transducers.

DETAILED DESCRIPTION OF THE INVENTION

Figure 1:
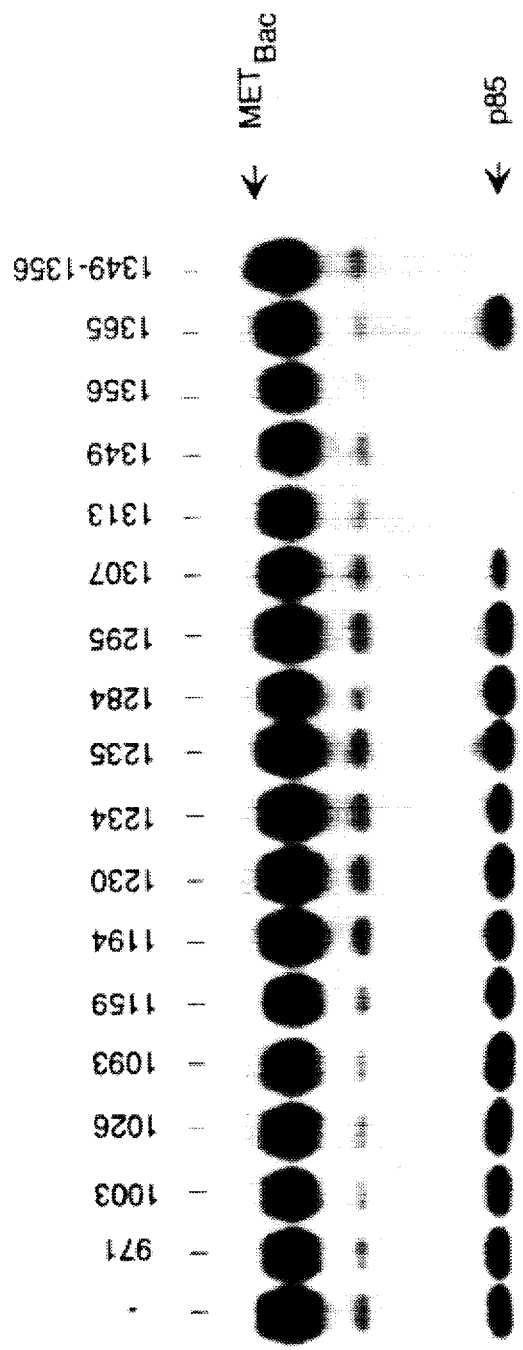

The peptides of the present invention are generally tyrosine-containing molecules representing sites of tyrosine phosphorylation. The peptides have a length of, for example, 4 to 20 amino acids, for example 8 to 12 amino acids.

The peptides generally reproduce potential recognition motifs for the SH2 domains of intracellular signal transducers.

The peptides may have from 4 to 20 amino acids and have the sequence $X_N$-YVN(or H)V-$X_C$ (SEQ. ID NOS: 5 and 6) wherein $X_N$ and $X_C$ are each sequences of from 0 to 16 amino acids.

Preferably, $X_N$ and $X_C$ are sequences which flank one of the YVN(or H)V (SEQ. ID NOS: 3 and 4) sequences in the HGF/SF receptor and Shc protein. The interaction of a transducer with activated tyrosine kinase receptor allows recruitment and activation of the transducer itself.

The activation of the HGF/SF receptor may be physiological (i.e. as a result of ligand binding), or constitutive (i.e. the receptor is permanently activated even in the absence of ligand). Constitutive activation may occur in a form of the receptor not having the extracellular ligand binding domain, for example in an oncogenic receptor or following a chromosomal translocation (as in the TPR-MET fusion described herein). Most intracellular signal transducers have been correlated to cell growth and to oncogenic transformation (Fantl,. W. J., et al., Cell. 69: 413–423 (1992); Reedijk, M., et al., Mol. Cell. Biol. 10: 5601–5608 (1990); Lowenstein, E. J. et al., Cell 70: 431–442 (1992)). Therefore, inhibition of the binding of intracellular signal transducers with activated tyrosine kinase receptor or of the binding between Shc protein and other transducers constitutes a means to inhibit cellular mitogenesis and motogenesis, and hence the peptide of the invention may counteract development of a tumor.

A preferred embodiment of the invention is a peptide selected from:

In the HGF receptor there is a potential recognition motif Tyr-Glu-Val-Met ($Y_{1313}$EVM) (SEQ. ID NO: 25), which could represent a binding site for PI 3-kinase.

Surprisingly, the experimental results reported hereinbelow show that although the synthetic phosphopeptide containing the consensus $Y_{1313}$EVM (SEQ. ID NO: 25) is capable of binding to PI 3-kinase, tyrosine 1313 can be eliminated from the receptor by site-directed mutagenesis without affecting PI 3-kinase binding. On the contrary, using both the synthetic phosphopeptides of the invention and receptor Tyr-Phe mutants the authors of the present invention have identified the binding sites for PI 3-kinase in the two phosphotyrosines in position 1349 and 1356, as demonstrated by inhibition data obtained using phosphopeptides H-Tyr*-Val-His-Val-Asn-Ala-Thr-Tyr-OH (SEQ. ID NO: 20), H-Tyr*-Val-Asn-Val-Lys-Cys-Val-Ala-OH (SEQ. ID NO: 22) and H-Tyr*-Val-His-Val-Asn-Ala-Thr-Tyr*-Val-Asn-Val-Lys-OH (SEQ. ID NO: 21).

These residues thus identify Tyr-Val-(Asn or His)-Val [YV(N or H)V] (SEQ. ID NOS: 3 and 4) as a novel recognition motif for PI 3-kinase and the corresponding phosphopeptides can be usefully employed as inhibitors of the binding of the HGF receptor with PI 3-kinase.

A particularly preferred embodiment of the present invention is therefore a phosphopeptide having the formula H-Tyr*-Val-His-Val-Asn-Ala-Thr-Tyr-OH (SEQ. ID NO: 20) or H-Tyr*-Val-Asn-Val-Lys-Cys-Val-Ala-OH (SEQ. ID NO: 22) or H-Tyr*-Val-His-Val-Asn-Ala-Thr-Tyr*-Val-Asn-Val-Lys-OH (SEQ. ID NO: 21), where in Tyr* indicates a residue of phosphorylated tyrosine.

A further preferred embodiment of the invention is peptide H-Asp-Asp-Pro-Ser-Tyr*-Val-Asn-Val-Gln-OH (SEQ. ID NO: 27) (DDPSY*VNVQ) wherein Tyr* (Y*) represents phosphorylated or unphosphorylated tyrosine.

| Position of Tyrosine in HGF/SF receptor sequence | Phosphopeptides three letter code | one letter code |
|---|---|---|
| (SEQ. ID NO: 7) 971 | H—Tyr*—Asp—Ala—Arg—Val—His—Thr—Pro—OH | Y*DARVHTP |
| (SEQ. ID NO: 8) 1003 | H—Tyr*—Arg—Ala—Thr—Phe—Pro—Glu—Asp—OH | Y*RATFPED |
| (SEQ. ID NO: 9) 1026 | H—Tyr*—Pro—Leu—Thr—Asp—Met—Ser—Pro—OH | Y*PLTDMSP |
| (SEQ. ID NO: 10) 1093 | H—Tyr*—His—Gly—Thr—Leu—Leu—Asp—Asn—OH | Y*HGTLLDN |
| (SEQ. ID NO: 11) 1159 | H—Tyr*—Met—Lys—His—Gly—Asp—Leu—Arg—OH | Y*MKHGDLR |
| (SEQ. ID NO: 12) 1192 | H—Tyr*—Leu—Ala—Ser—Lys—Lys—Phe—Val—OH | Y*LASKKFV |
| (SEQ. ID NO: 13) 1230 | H—Tyr*—Asp—Lys—Glu—Tyr—Tyr—Ser—Val—OH | Y*DKEYYSV |
| 971 | H—Tyr*—Asp—Ala—Arg—Val—His—Thr—Pro—OH | Y*DARVHTP |
| 1234 | H—Tyr*—Tyr—Ser—Val—His—Asn—Lys—Thr—OH | Y*YSVHNKT |
| 1235 | H—Tyr*—Ser—Val—His—Asn—Lys—Thr—Gly—OH | Y*SVHNKTG |
| 1284 | H—Tyr*—Pro—Asp—Val—Asn—Thr—Phe—Asp—OH | Y*PDVNTPD |
| 1295 | H—Tyr*—Leu—Leu—Gln—Gly—Arg—Arg—Leu—OH | Y*LLGGRRL |
| 1307 | H—Tyr*—Cys—Pro—Asp—Pro—Leu—Tyr—Glu—OH | Y*CPDPLYE |
| 1313 | H—Tyr*—Glu—Val—Met—Leu—Lys—Cys—Trp—OH | Y*EVMLKCW |
| 1349 | H—Tyr*—Val—His—Val—Asn—Ala—Thr—Tyr—OH | Y*VMVNATY |
| 1349–1356 | H—Tyr*—Val—His—Val—Asn—Ala—Thr—Tyr*—Val—Asn—Val—Lys—OH | Y*VNVMATY*VNVK |
| 1356 | H—Tyr*—Val—Asn—Val—Lys—Cys—Val—Ala—OH | Y*VNVKCVA |
| 1365 | H—Tyr*—Pro—Ser—Leu—Leu—Ser—Ser—Glu—OH | Y*PSLLSSE |

Positions 971–1365 (which refer to eleven sequences) correspond to SEQ. ID NOS: 7 and 14–23, respectively.
wherein Tyr* indicates a phosphorylated or unphosphorylated tyrosine residue.

Of the known intracellular signal transducers, PI 3-kinase has been demonstrated to bind HGF receptor either in vitro or in vivo upon ligand stimulation.

Previous work, carried out with the PDGF receptor, had shown that the four amino acids sequence Tyr-Xxx-Xxx-Met (YXXM) (SEQ. ID NO: 24), wherein Xxx or X represents any amino acid residue in the three letter code or one-letter code respectively, constitutes the canonical consensus sequence for PX 3-kinase binding.

The peptides of the invention may be provided in the form of pharmaceutically acceptable salts. Suitable salts include base salts such as alkali metal salts (e.g. sodium or potassium salts) and ammonium salts; and acid addition salts such as hydrochloride and acetate salts.

The peptides of the invention can be synthesized according to standard method such as those described in Escobedo, J. A., et al., Mol. Cell. Biol. 11: 1125–1132 (1991) or Turck, C. W. Peptide Res. 5: 156–160 (1992), for example using a protected prephosphorylated tyrosine residue.

In particular the peptides can be prepared by liquid or solid-phase methodologies known to those skilled in the art. (Schroeder et al., "The Peptides", Vol. I, Academic Press 1965, or Bodanszky et al., "Peptide Synthesis", Interscience Publishers, 1966, or McOmie (ed.) "Protective Group in Organic Chemistry", Plenum Press, 1973, or Barany et al., "The Peptides: Analysis, Synthesis, Biology", 2, Chapter 1, Academic Press, 1980).

Thus, the invention includes a process for preparing a peptide of the invention, which process comprises chemically synthesizing the peptide from single amino acids and/or preformed peptides of two or more amino acid residues.

When it is wished to prepare a peptide in which a tyrosine residue is phosphorylated, a prephosphorylated protected tyrosine residue may be introduced during a solid phase synthesis, or a tyrosine residue of a protected preformed peptide may be phosphorylated while the peptide is attached to a solid support.

In the case of solid-phase synthesis any manual or automatic peptide synthesizer can be used and the peptides can be assembled in a stepwise manner on a resin support using either Boc or Fmoc strategies.

All the reagents used as starting materials are on the market or may be produced and purified in accordance with methods known in the art.

When preparing a phosphopeptide, in order to avoid cleavage of the phosphate group during deprotection of the protected peptides, a solution of trifluoromethane sulfonic acid-trifluoroacetic acid containing a suitable mixture of scavangers is used.

The deprotected peptides are purified by reverse phase high performance liquid chromatography on a C18-Vydac column (Hesperia Calif.) in 0.1% trifluoroacetic acid by using a linear gradient of acetonitrile, and are isolated by lyophilization. All phosphopeptides are obtained as polihydrated polytrifluoroacetates. The peptide content of all products is 65 to 90% and the chromatographic purity is more than 95% by HPLC peak relative integration at $\lambda=225$ nm. Amino acid analysis were carried out on acid hydrolysates (110° C. for 22 h in 6N HCl+0.1% phenol). Alternatively a peptide containing a non-phosphorylated tyrosine can be first synthesized and subsequently a phosphate group can be introduced on the tyrosine residue either enzymatically or by chemical methods (in such a case the other functions susceptible of reaction with the phosphorylating agent must be suitably protected).

In this specification, the abbreviations used for amino acids and protecting groups are based on recommandations of the IUPAC-IUB Commission on Biochemical Nomenclature (see Eur. J. Biochem., vol 138, 9–37, 1984). In particular, the following abbreviations were used throughout the text: Boc, t-butyloxycarbonyl; tBu, t-butyl; Bzl, benzyl; ClZ, 4-chloro benzyloxycarbonyl; DPCDI, diisopropylcarbodiimide; DCM, dichloromethane; DMF, dimethylformamide; Dnp, dinitrophenyl; Fmoc, 9-fluorenylmethoxycarbonyl; RP-HPLC, reverse phase high performance liquid chromatography; Trt, trityl.

The capacity of the phosphopeptides of the invention to inhibit the binding of intracellular transducers to the tyrosine kinase receptor or to Shc protein can be assessed by competition experiments as shown in the experimental section for the binding to the tyrosine kinase receptor.

A further demonstration of the biological significance of the autophosphorylation sites on the tyrosine kinase receptor is provided by the focus formation assay described in the experimental section.

In particular, this assay demonstrates how the transforming activity of the oncogenic form of the HGF receptor can be efficiently inhibited by mutating the specific autophosphorylation sites under consideration (Tyr-Phe mutation).

A peptide reproducing one of the phosphorylation sites of HGF/SF receptor or Shc can then interfere with binding of transducers thus inhibiting the downstream transmission of the mitogenic and motogenic signal.

The peptides of the invention can therefore be used in the treatment of the human or animal body by therapy, for example in the treatment of a neoplastic disease.

The peptides of the invention are phosphorylated or unphosphorylated. The active form of the peptides is generally phosphorylated, but it may be advantageous to administer a peptide in unphosphorylated form and allow the peptide to become phosphorylated inside the body of the patient. This is because the peptides may be more easily taken up into cells when unphosphorylated.

The peptides of the invention may be administered to a patient by any convenient parenteral route as such or properly conjugated in order to increase enzymatic stability and cell permeability.

The choice of whether subcutaneous, intravenous or intramuscular administration is adopted; of the dose; of the frequency of administration depends upon a variety of factors. These factors include the purpose of the administration, the age and weight of the patient being treated and the condition of the patient. A therapeutically effective amount is given. Typically, however, the peptide is administered in an amount of from 10 to 1000 μg per dose, more preferably from 50 to 500 μg per dose, for each route of administration.

The peptide may be formulated in a pharmaceutical composition. The pharmaceutical composition also comprises a pharmaceutically acceptable carrier or diluent. Any appropriate carrier or diluent may be employed, depending upon the route of administration.

The following Example illustrates the invention.

In the accompanying drawings:

FIG. 1. Inhibition of binding of p85 to MGF/SF receptor by tyrosine-phosphorylated peptides. Recombinant HGF/SF receptor was purified by immunoprecipitation from baculovirus-infected Sf9 cells using a rabbit polyclonal antiserum and phosphorylated with cold ATP. Lysates of Sf9 cells expressing p85 were pre-incubated with each of the phosphopeptides (10 μM). The lysates were then allowed to associate with immobilized recombinant HGF/SF receptors. Following association the complex was washed and receptor-bound p85 was detected by an in vitro kinase assay, as described in Materials and Methods of Example 4. The phosphopeptides are identified by the number of the amino terminal tyrosine.

Figure 2A:
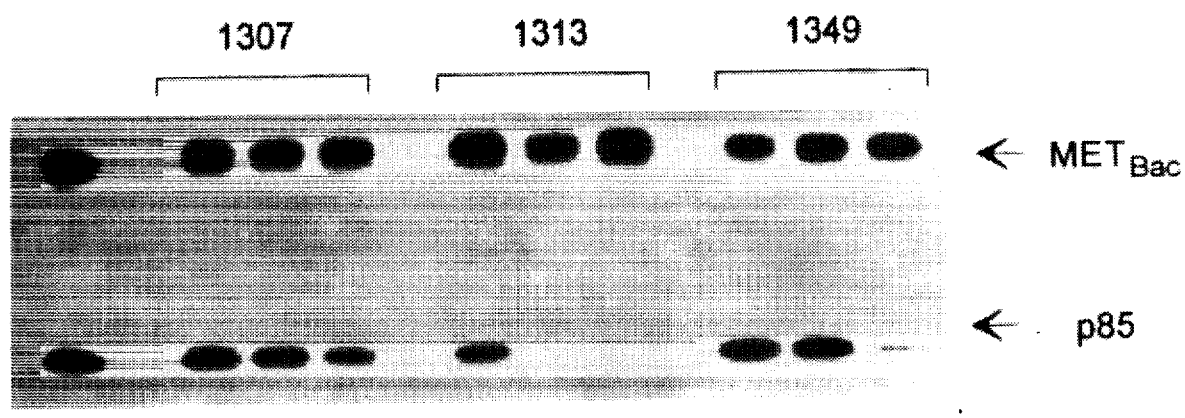
Figure 2B:
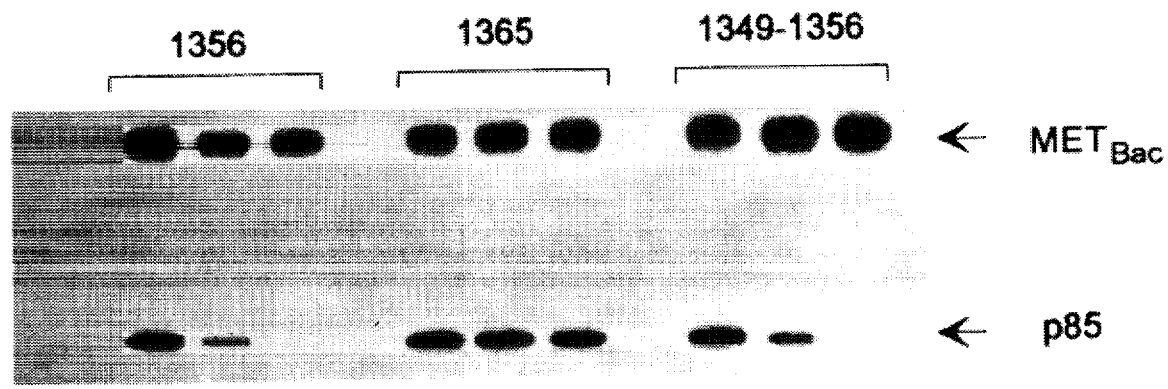

FIG. 2. Inhibition of binding of p85 to HGF/SF receptor with different concentrations of tyrosine-phosphorylated peptides. The phosphopeptides which efficiently out-competed p85 binding to the HGF/SF receptor (FIG. 1) were used at increasing concentrations (10 nM, 100 nM, 1 μM from left to right) to define their relative affinities for p85. Conditions of the experiment were as in FIG. 1. Phosphopeptide 1365 was used as a negative control for p85 interaction.

Figure 3:
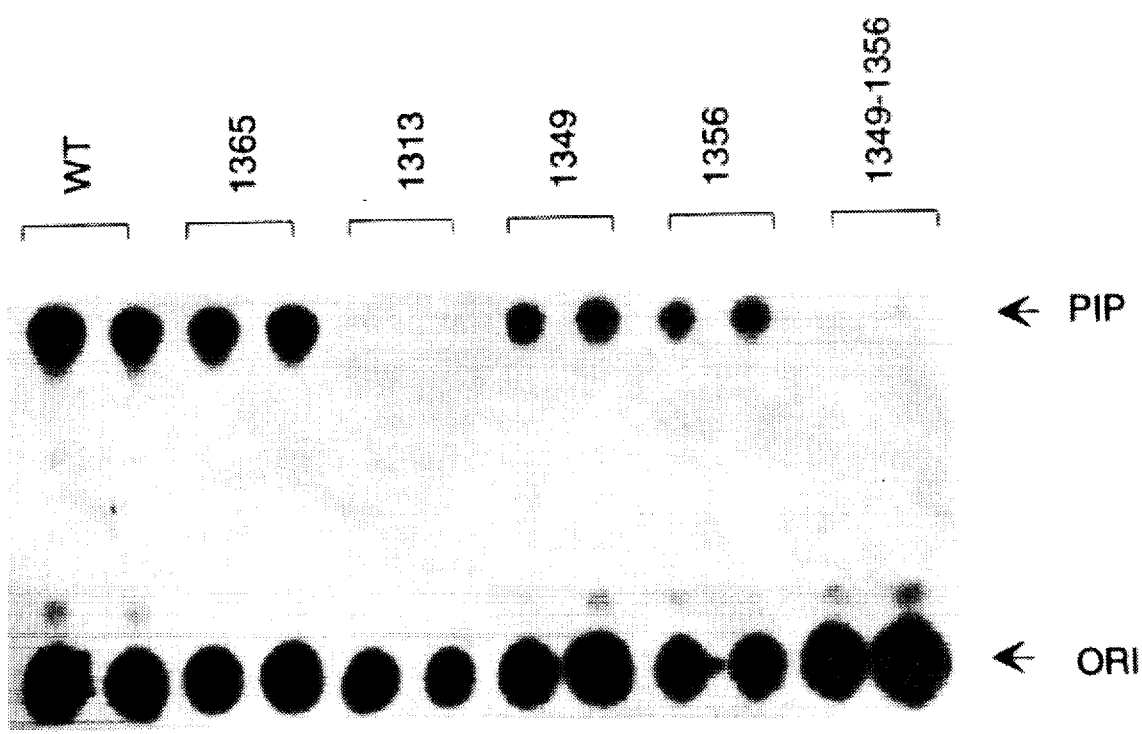
Figure 5A:
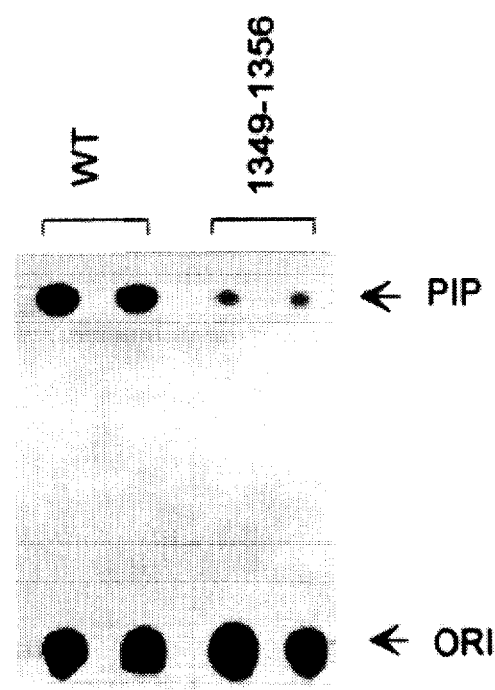
Figure 5B:
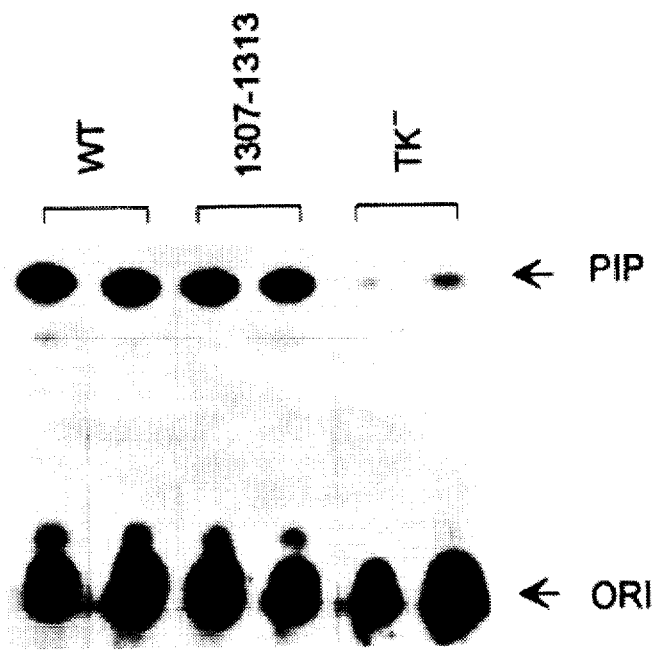
Figure 5C:
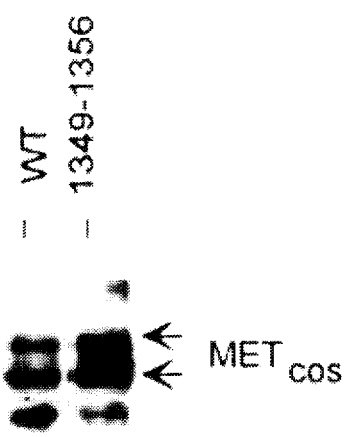
Figure 5D:
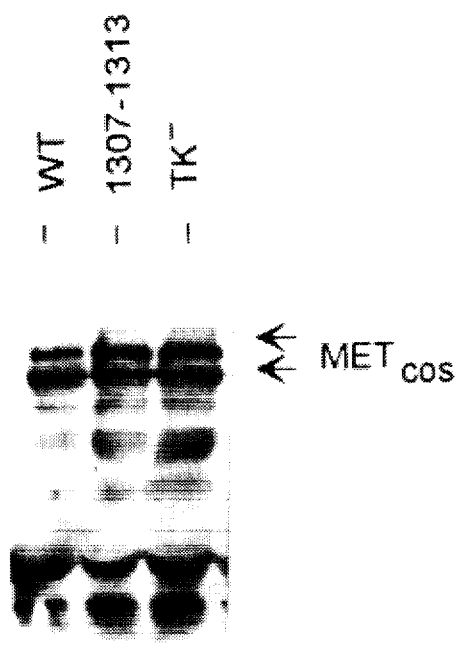

FIG. 3. Inhibition of binding of PI 3-kinase holoenzyme to HGF/SF receptor by tyrosine-phosphorylated peptides. The phosphopeptides which efficiently out-competed p85 (FIG. 1) were assayed for the ability to interfere with binding of the PI 3-kinase holoenzyme to the HGF/SF receptor. Cytosolic extracts from three days-starved A549 cells were pre-incubated with each of the phosphopeptides (10 µM) prior to incubation with the immobilized recombinant HGF/SF receptor. The presence of receptor-associated PI 3-kinase in the immunocomplexes was determined by PI 3-kinase activity assay, as described in Materials and Methods of Example 4. The position of the phosphatidylinositol-3-phosphate (PIP) product of the PI 3-kinase reaction is indicated.

FIG. 4. Effects of Tyr-Phe mutations on the interaction of HGF/SF receptor with p85. COS 7 cells were transfected with plasmids encoding wild type HGF/SF receptor (wt) or receptors in which the tyrosine codon at the indicated position was converted to a phenylalanine codon individually, or in combination. COS 7 cells express endogenous HGF/SF receptor. However, the simian protein is not recognized by a monoclonal antibody directed against the carboxyl-terminal human-specific peptide. These antibodies were used to selectively immunoprecipitate the human HGF/SF receptor from transfected COS 7 cells. Immobilized pre-phosphorylated receptors were incubated with lysates of Sf9 cells expressing p85. In panel A both the receptor and p85 were labelled by an in vitro kinase assay as described in Materials and Methods of Example 4. In panel B the presence of p85 in the receptor immune-complex was determined by immunoblot using anti-p85 monoclonal antibodies.

FIG. 5. In vivo effect of Tyr-Phe mutations on the interaction of the HGF/SF receptor with the PI 3-kinase holoenzyme. COS 7 cells expressing wild type or mutated receptors were stimulated with HGF/SF and lysed. Receptors were immunoprecipitated with human-specific monoclonal antibodies. In panel A and B the presence of the receptor-associated PI 3-kinase was determined by PI 3-kinase activity assay, as described in Materials and Methods of Example 4. The position of the phosphatidylinositol-3-phosphate (PIP) product of the PI 3-kinase reaction is indicated. Panel C and D show by immunoblot (using human-specific monoclonal antibodies) that the samples tested for PI 3-kinase activity contained equivalent amounts of recombinant receptor. The TK receptor mutant has been obtained converting the aspartic acid at position 1204 to an asparagine residue. This results in a kinase-inactive HGF/SF receptor.

Figure 6A:
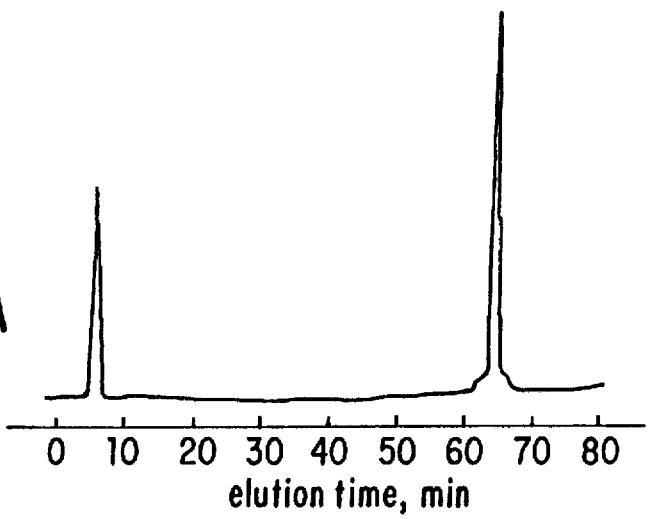
Figure 6B:
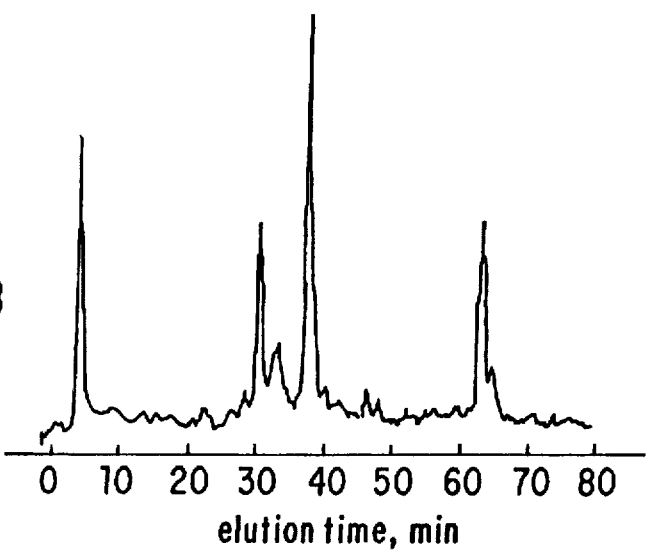
Figure 6C:
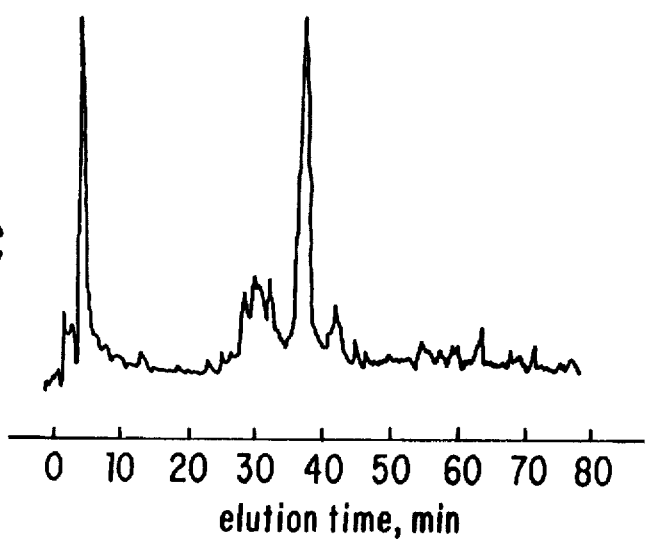

FIG. 6. Identification of $Y_{1349}$ and $Y_{1356}$ as in vitro phosphorylation sites in the HGF/SF receptor by tryptic phosphopeptide mapping. Profile A shows the HPLC analysis at 214 nm of a synthetic non-phosphorylated peptide (I24K), which corresponds to the tryptic peptide containing tyrosine $Y_{1349}$ and $Y_{1356}$ in the HGF/SF receptor. I24K elutes from the HPLC column after 65 minutes. B and C show the radio-HPLC elution profiles of tryptic phosphopeptides derived from in vitro [$\gamma$-$^{32}$P]ATP-phosphorylated wild type receptor (B) and the $Phe_{1349-1356}$ receptor mutant (C).

Figure 7A:
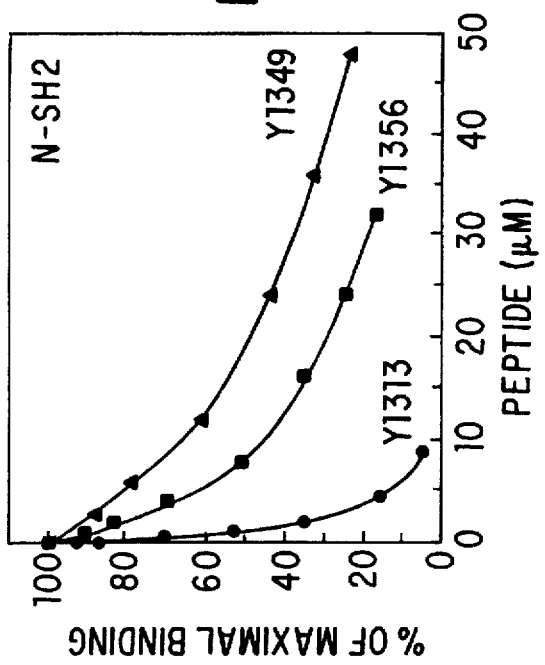

FIG. 7. Evaluation of the relative affinities of phosphotyrosine 1313, 1349 and 1356 for the N- and C-SH2 domains of p85. Affinities were determined by biospecific interaction analysis with the BIAcore instrument (Jonsson, U., Fagerstam, L., Roos, H., Ronnberg, J., Sjolander, Stenber, E., Stahlberg, R. Urbaniczky, C., Ostlin, H., and Malmquist. 1991. Surface plasmon reasonance and microfluidics for real time biospecific interaction analysis. Biotechniques 11: 520–527; Jonsson, U. and M. Malmquist. 1992. Real time biospecific analysis. The integration of surface plasmon reasonance detection, general biospecific interface chemistry and microfluidics into one analytical system p. 291–336. In F. Turner (ed), Advances in Biosensors, vol. 2 JAI Press, London; Karlsson, R., Michaelsson, A., and L. Mattsson. 1991. Kinetic analysis of monoclonal antibody-antigen interactions with a new biosensor based analytical system. J. Immunol. Meth. 145: 229–246).

Relative affinities were determined by measuring the ability of the phosphopeptides to inhibit the interaction of the SH2 domains with an immobilized phosphopeptide (DMSKDESVDY*VPMLDMK) (SEQ. ID NO: 26) which includes $Y_{751}$ in the human PDGF receptor. Panel A and B show the results of these measurements, expressed as % inhibition of binding to phosphopeptide Y751. Panel C, shows the phosphopeptide concentrations necessary to reach half-maximal inhibition of binding.

FIG. 8. Focus Formation Assay with different TPR-MET constructs. In TPR-MET$^{1349}$, TPR-MET Phe$^{1356}$ and TPR-MET Phe$^{1349-1356}$ the tyrosine residues corresponding to $Tyr_{1349}$ and/or $Tyr_{1356}$ of the HGF/SF receptor were mutagenized to phenylalanine.

FIG. 9. SF/HGF induces phosphorylation of Shc and association with SF/HGF receptor and Grb2. A549 cells, either control or expressing the $Y^{317} \rightarrow F$ mutant Shc cDNA (A549/Y317F), were grown to confluence, serum starved for 24 hours and lysed. Where indicated (+), cells were stimulated for 5' with 200 U/ml of pure SF/HGF. Immunocomplexes, precipitated with the first antibody (IPP), were resolved on 9% SDS-PAGE and analyzed by immunoblot with a second antibody (WB), as indicated. Arrows point the endogenous Shc isoforms (p46, p52, p56), the SF/HGF receptor β chain (p145), the transfected tagged mutant Shc isoforms (p53 and p58) and the Grb2 protein (p23).

FIG. 10. Association and tyrosine phosphorylation of Shc are dependent on SF/HGF receptor kinase activity. Lysates of COS-1 cells transiently expressing the cDNAs of wild-type SF\HGF receptor (WT) or of a kinase-defective receptor mutant (LYS$^-$) were immunoprecipitated with either anti-Met monoclonal antibody (A. and B.) or an anti-Shc polyclonal sera (C. and D.), western blotted and probed with either anti-Met or anti P-Tyr antibodies, as indicated. Arrows indicate the precursor protein (p170) that in COS-1 cells is the predominant, fully functional, form of the SF/HGF receptor (Ponzetto et al., Mol. Cell. Biol. 13: 4600–4608 (1993)); p46, p52 and p56 are Shc isoforms.

Figure 11A:
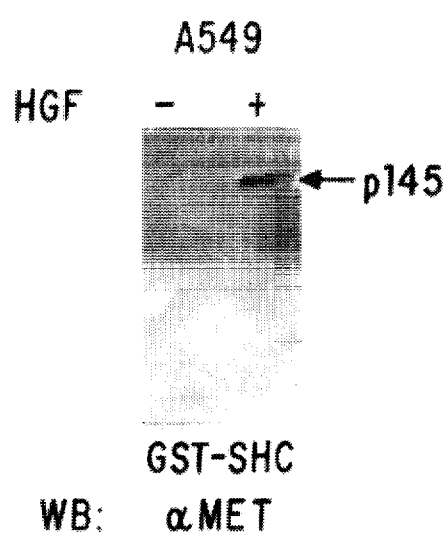
Figure 11B:
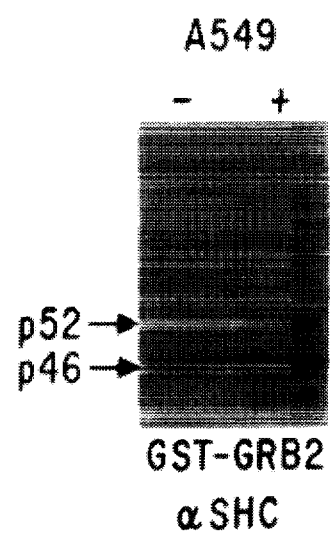

FIG. 11. Binding of Shc and Grb2 SH2 domains to proteins solubilized from SF/HGF treated cells. Lysates were prepared from confluent monolayers of unstimulated (−) or SF/HGF stimulated (+) A549 cells. Association experiments were carried out incubating total cell protein with recombinant GST-SH2.Shc (A.) or GST-SH2.Grb2 (B.) immobilized onto glutathione Sepharose. The bound proteins were eluted and analyzed in western blot using the indicated antibodies.

Figure 12:
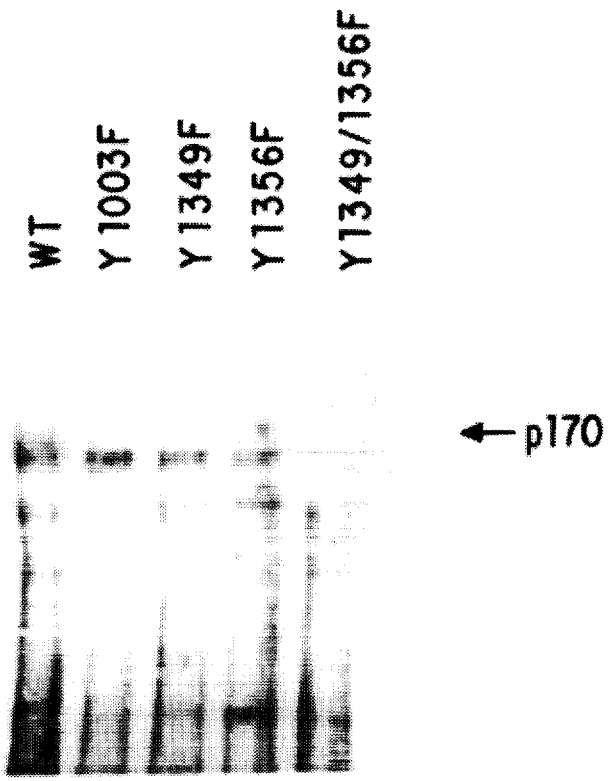

FIG. 12. Mapping of Shc binding sites on the SF/HGF receptor. COS-1 cells expressing SFHGF receptors, either (WT) or mutated Y→F at the residues indicated on the top of each line, were co-immunoprecipitated with anti-Shc antibodies, blotted and revealed by anti-Met antibodies. The arrow indicates the receptor precursor (p170).

Figure 13:
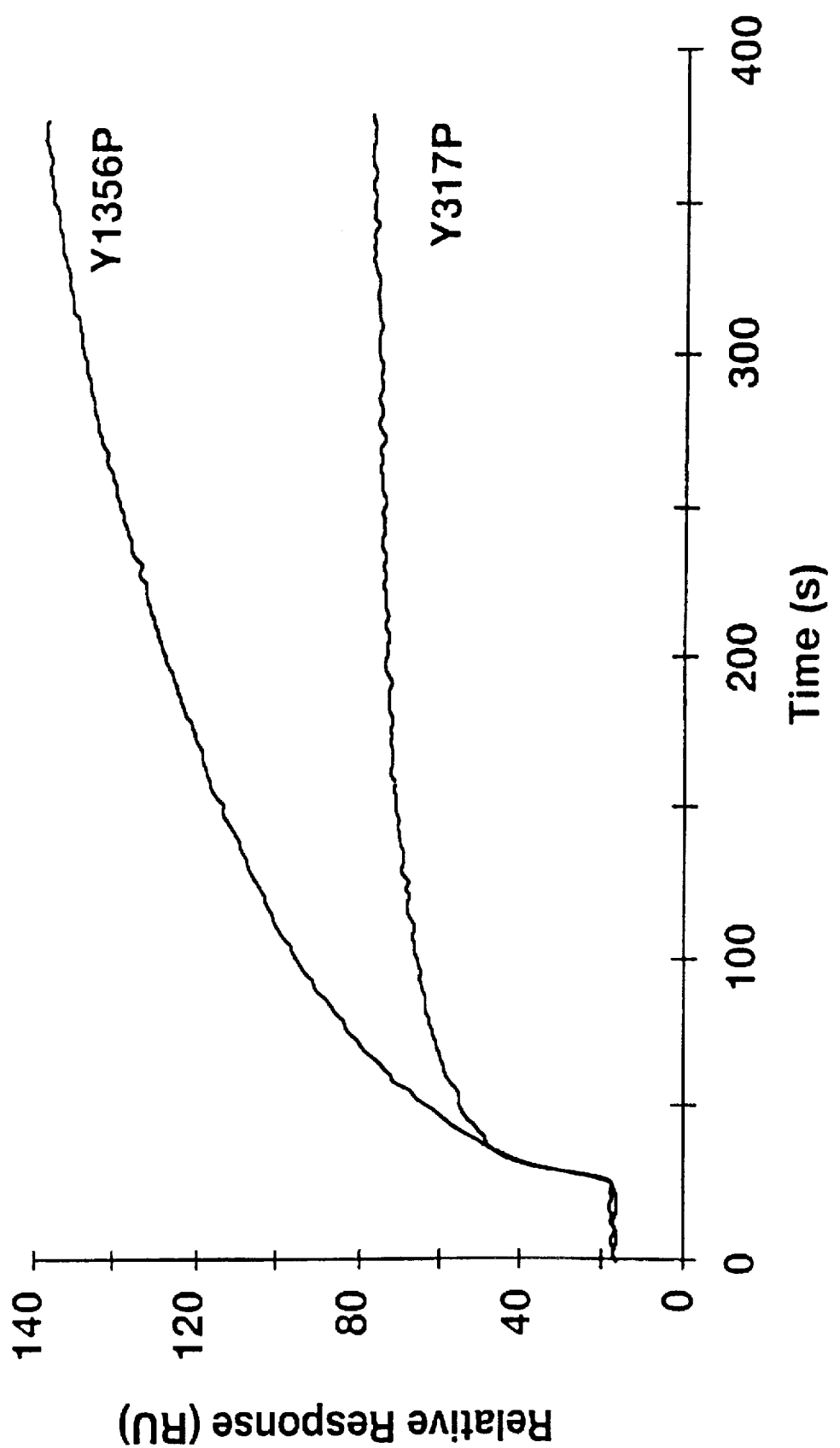

FIG. 13. The Shc SH2 domain binds to the docking site of the SF/HGF receptor ($Y^{1356}$) but not to its own ($Y^{317}$). The same concentration of Shc-SH2 was injected over two biosensor surfaces on which two phosphopeptides had been immobilised. Y1356P is derived from the sequence VNATY$^{1356}$VNVK (SEQ. ID NO: 28) of the receptor tail; Y317P is derived from the sequence DDPSY$^{317}$VNVQ (SEQ. ID NO: 27). Note that both peptides contain the same core (YVNV) (SEQ. ID NO: 3) but different upstream sequences. The initial rapid increase in the response is due to the "bulk effect" of the injected solution.

Figure 14A:
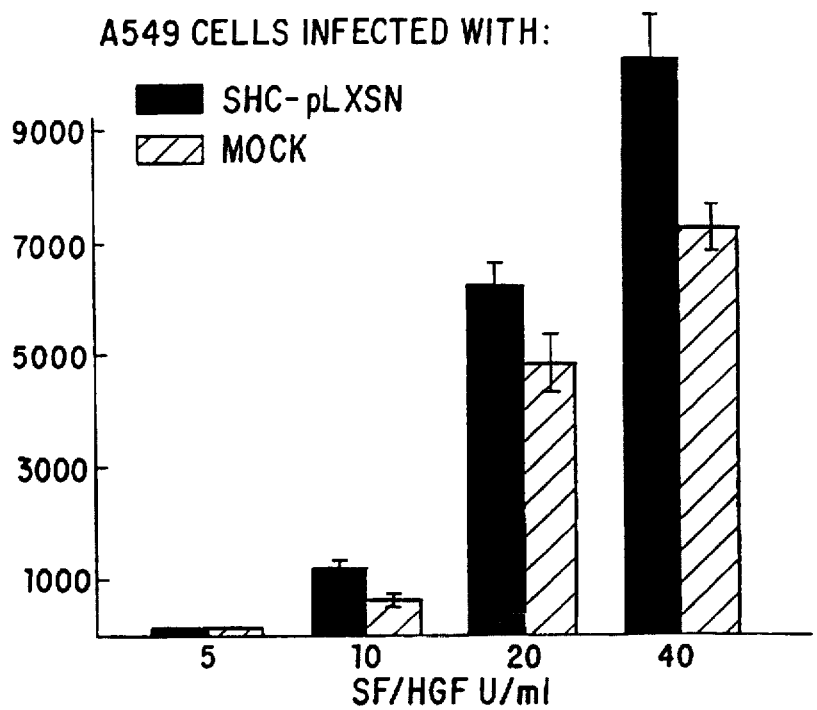
Figure 14B:
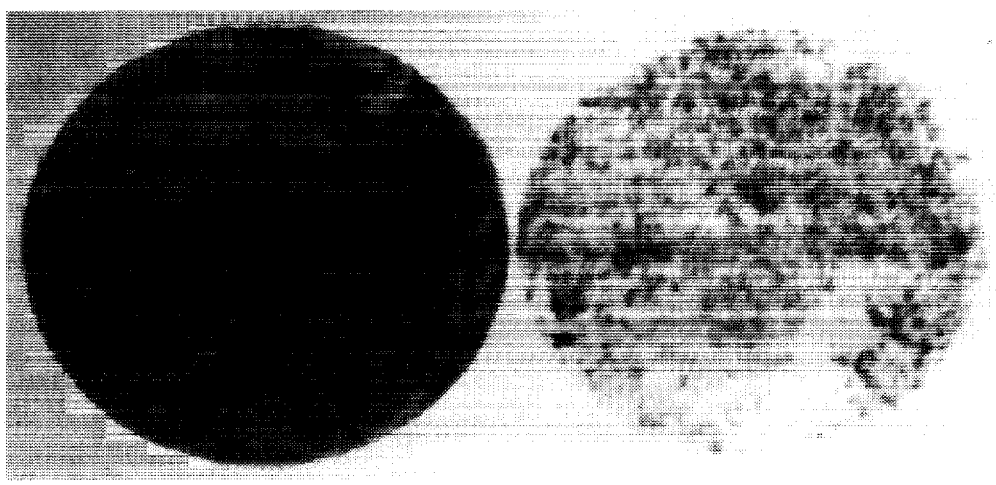
Figure 15A:
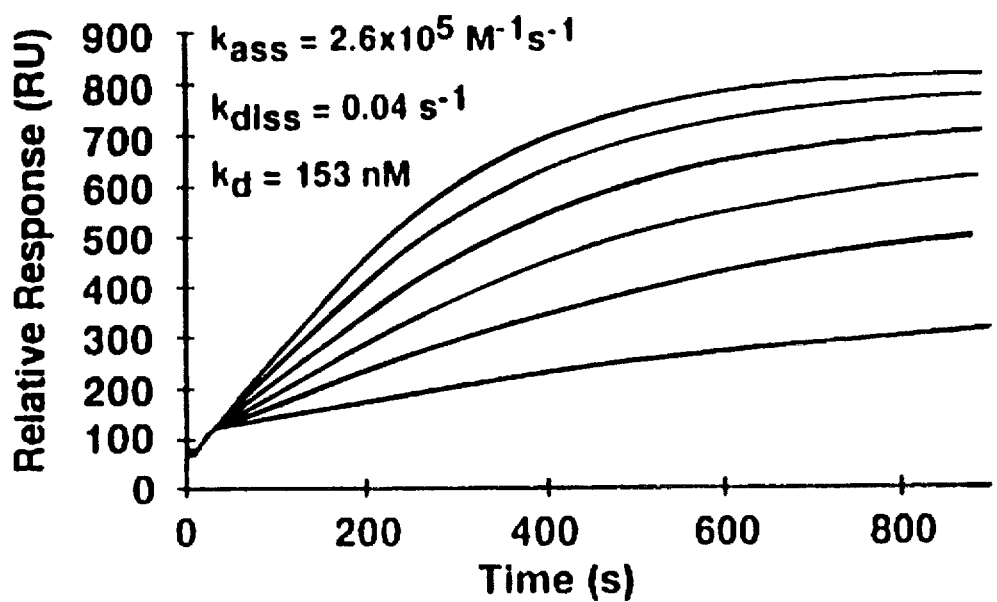
Figure 15B:
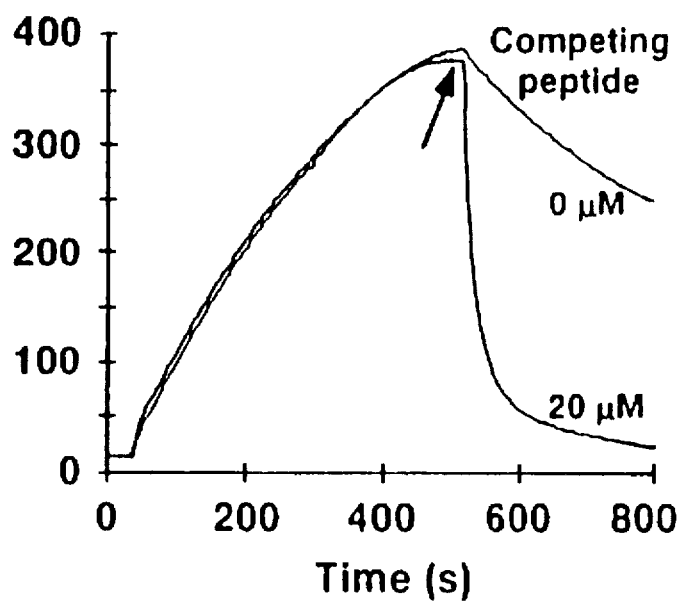
Figure 15C:
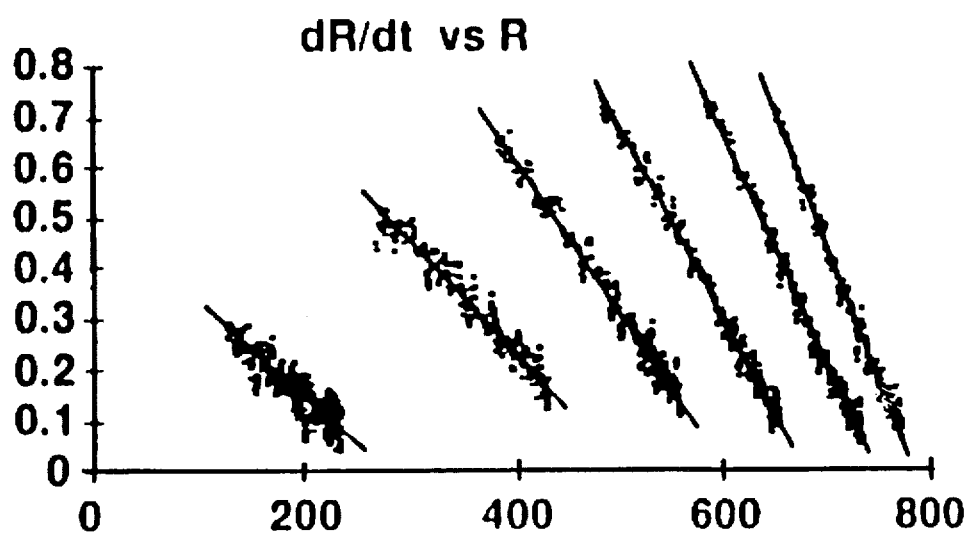
Figure 15D:
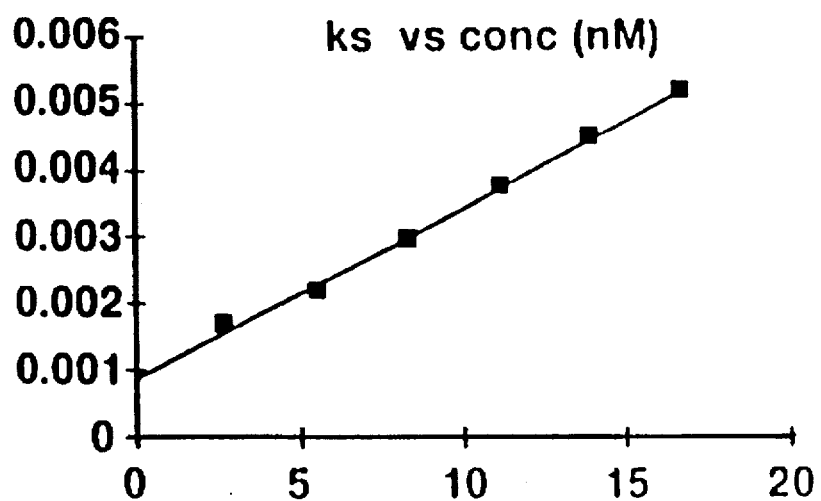

FIG. 14. Overexpression of Shc enhances the motogenic response to SF/HGF. Blind-well Boyden chambers were assembled with polycarbonate filters (8 μm pores) coated with gelatine. The cells were labelled with 5-[$^{125}$I]iodo-2'-deoxyuridine (see Methods) and plated in the upper chamber. The lower chamber was filled with serum-free medium supplemented with the indicated concentrations of purified SF/HGF. After 6 h of incubation at 37° C., cells attached to the upper side of the filters were mechanically removed; the cells migrated to the lower side of the filter were fixed and quantitated in a γ-counter (Y axes: CPM bound). The lower panel shows a low-magnification micrograph picture (4x) of cells migrated to the lower side of the filters in the presence of 40 U/ml of SF/HGF. Cells were either infected with a retrovirus carrying the SHC cDNA (SHC-pIXSN), or with the empty virus (MOCK).

FIG. 15. The Grb2 SH2 domain binds to the $Y^{317}$ docking site of Shc. Panel A: sensorgrams obtained by injection of a range of Gst-SH2.Grb2 concentrations over the immobilised phosphopeptide derived from the Shc sequence DDPSY$^{317}$VNVQ (SEQ. ID NO: 27). Panel B: effect of competing peptide on the dissociation rate. At the end of the Grb2 injection, buffer or 20 M of non-biotinylated phosphopeptide were injected. Panel C: analysis of the data shown in panel A. The figure on the left is a plot of the rate of binding versus the relative response for the six different sensorgrams. In the figure on the right, the slopes of each line are plotted against the concentration: the new slope gives the value of the association rate constant.

Figure 16:
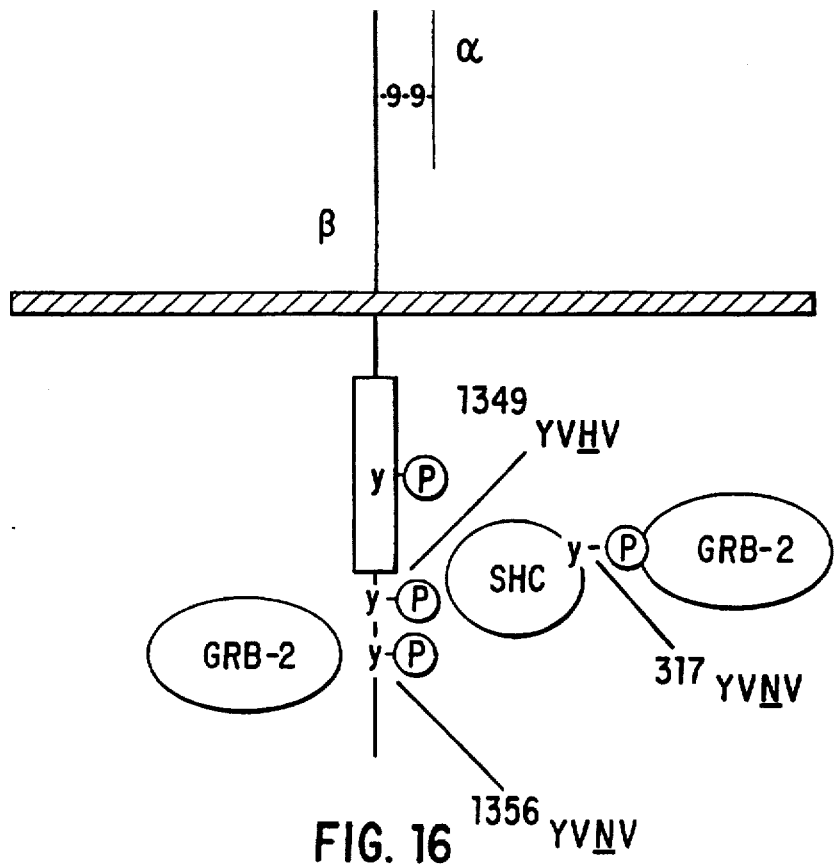

FIG. 16. A model of the interactions between the SF/HGF receptor and the SH2 containing adaptor molecules Shc and Grb2. Grb2 binds with high affinity with the docking site $Y^{1356}$VNV (SEQ. ID NO: 3) on the receptor tail. The adaptor molecule Shc can interact with either phosphotyrosine $Y^{1349}$ or $Y^{1356}$. Upon binding, Shc is transphosphorylated by the receptor on $Y^{317}$, re-creating a high affinity docking site for Grb2. The receptor may thus activate the motogenic response through the Shc pathway, without interfering with the Ras-mediated mitogenic response driven by Grb2-SoS.

EXAMPLE 1

Preparation of
H-Tyr*-Val-His-Val-Asn-Ala-Thr-Tyr-OH (SEQ. ID NO: 20) (Formula I)

0.89 g (0.5 mmol.) of Fmoc-Tyr (tBu)-4-(oxymethyl) phenoxymethyl-copoly(styrene-1% divinylbenzene) resin (0.56 mmol/g) were subjected to the following cycle, steps (1) to (5), of treatments:

(1) DMF
(2) piperidine (20%) in DMF
(3) DMF
(4) preformed 1-hydroxybenzotriazole ester (2.0 mmol) of Fmoc-amino acid in DMF Volumes of washes and reagents were 10 to 20 ml.

Each step was repeated as many times as necessary for either complete reaction of the resin (steps 2,4) or complete displacement of the previous reagent from the resin (steps 1, 3, 5). Samples of resin were taken after each cycle and checked for completeness of reaction by a ninhydrin test. 1-hydroxybenzotriazole esters of Fmoc-amino acids were formed just prior to use by reacting Fmoc-amino acid (2.0 mmol.), 1-hydroxybenzotriazole (2.0 mmol.) and DPCDI (2.0 mmol.) in DMF.

The cycle of reactions, (1) to (5), was repeated for each amino acid residues such as to provide the sequence of formula I.

The following protected amino acids were added in the order: Fmoc-Thr(tBu)-OH, Fmoc-Ala-OH, Fmoc-Asn-OH, Fmoc-Val-OH, Fmoc-His(Trt)-OH, Fmoc-Val-OH and Boc-Tyr (PO3Bzl2)-OH.

After the last cycle the peptidyl resin was washed several times with DCM and dried.

A weight gain of 0.54 g was obtained with respect to the starting resin.

1.0 g of the peptidyl resin was stirred with 20 ml of a mixture of trifluoromethanesulfonic acid/trifluoroacetic acid/dimethyl-sulfide/ethanedithiol (20:50:3:3:1) for 3 h at 0° C. Deprotected peptide was precipitated with 1 liter of diethylether and collected by filtration.

The crude peptide was purified by RP-HPLC on a C18-Vydac (Hesperia, Calif.) column (2,2×25 cm) in 0.1% trifluoroacetic acid using a linear gradient of acetonitrile from 0–65% over 90 min.

Fractions containing the product in pure form were combined, the acetonitrile was evaporated in vacuo and the remaining solution was lyophilized. It was obtained 132 mg of the compound of formula I with chromatographic purity (HPLC) of 95.7%.

Amino acid ratios: Ala 1(1); Asp 1.07(1); His 0.96(1); Thr 0.91(1); Tyr 1.88(2); Val 2.03(2).

Peptide content: 73.7%.

FAB mass spectroscopy; m/z 1044.4 [M-H]$^-$

EXAMPLE 2

Preparation of
H-Tyr*-Val-Asn-Val-Lys-Cys-Val-Ala-OH (SEQ. ID NO: 22) (Formula II)

Starting from 0.5 mmol of Fmoc-Ala-4-(oxymethyl) phenoxymethyl-copoly(styrene-1% divinylbenzene)resin and adding the protected amino acids in the following order: Fmoc-Val-OH, Fmoc-Cys(Trt)-OH,Fmoc-Lys(Boc)-OH, Fmoc-Val-OH, Fmoc-Asn-OH, Fmoc-Val-OH, Boc-Tyr-OH, the dephosphopeptide was assembled on the resin in the same manner as described in the example 1.

After the last cycle the phosphorylation of Tyr residue was obtained directly on the peptide still attached on the resin by treatment of the peptidyl resin with a solution of 30 eq. of 1H-tetrazole and 10 eq. of di-ter-butyl-N,N-diisopropylphosphoramidite in DMF for 1 h at 25° C. and subsequently with 20 eq. of ter-butylhydroperoxide in toluene for 1 h at 25° C. The cleavage, the protecting groups removal and the purification of crude product were carried out on 1.0 g of peptidyl resin as described in example 1.

Amino acid ratios: Ala 1(1); Asp 1.02(1); Cys nd(1); Lys 0.99(1); Tyr 0.95(1); Val 2.98(3).

Peptide content: 68.9%.

FAB mass spectroscopy: m/z 973.4 [M-H]$^-$

EXAMPLE 3

Preparation of
H-Tyr*-Val-His-Val-Asn-Ala-Thr-Tyr*-Val-Asn-Val-Lys-OH (SEQ. ID NO: 21) (Formula III)

0.74 g (0.5 mmol) of Boc-Lys (ClZ)-4-(oxymethyl) phenylacetamido-methyl-copoly(styrene-1% divinylbenzene) resin (0.68 mmol/g) were subjected to the following cycle, steps (1) to (7), of treatments:

(1) DCM
(2) trifluoroacetic acid (50%) in DCM
(3) DCM
(4) diisopropylethylamine (5%) in DMF
(5) DMF
(6) preformed 1-hydroxybenzotriazole ester (2.0 of Boc-amino acid in DMF
(7) DMF Each step was repeated as many times as necessary for either complete reaction of the resin (steps 2,4,6) or complete displacement of the previous reagent from the resin (1,3,5,7).

Samples of resin were taken after each cycle and checked for completeness of reaction by ninhydrin test.

1-hydroxybenzotriazole esters of Boc-amino acids were formed just prior to use by reacting Boc-amino acid (2.0 mmol.), 1-hydroxybenzotriazle (2.0 mmol.) and DPCD1 (2.0 mmol.) in DMF.

The cycle of reactions, (1) to (7), was repeated for each amino acid residue such as to provide the sequence of formula III.

The following protected amino acids were added in the order: Boc-Val-OH, Boc-Asn-OH, Boc-Val-OH, Boc-Tyr(PO3Bz12)-OH, Boc-Thr(Bzl)-OH, Boc-Ala-OH, Boc-Asn-OH, Boc-Val-OH, Boc-His(Dnp)-OH, Boc-Val-OH and Boc-Tyr(PO3Bz12)-OH.

At the completion of the synthesis of His(Dnp) protecting group was removed with 15 ml of 1M thiophenol in DMF directly on the peptide still attached on the resin, then the peptidyl resin was washed several times with DCM and dried.

1.51 g of peptidyl resin were obtained.

The cleavage, the protecting groups removal and the purification of the crude product were carried out on 1.0 g of starting peptidyl resin as described in example 1. It was obtained 196 mg of compound III with chromatographic purity (HPLC) of 95.9%.

Amino acid ratios: Ala 1(1); Asp 1.99(2); His 1.05(1); Lys 0.97(1); Thr 0.93(1); Tyr 1.85(2); Val 4.01(4).

Peptide content: 71.1%.

FAB mass spectroscopy: m/z 1564.62 [M-H]$^-$.

EXAMPLE 4

Materials and Methods

Reagents, cells, antibodies. All reagents, unless specified, were purchased from Sigma Chemical Co. Protein A covalently coupled to Sepharose was purchased from Pharmacia LKB Biotechnology Inc. All radioactive isotopes were purchased from Amersham Corp. A549 lung carcinoma cells and COS-7 cells, purchased from ATCC (CCL 185) (American Type Culture Collection), were grown in DMEM medium supplemented with 10% foetal calf serum (Flow Laboratories, Inc.) in a 5% $CO_2$-water-saturated atmosphere. *Spodoptera frugiperda* (Sf9) cells, from ATCC (CRL 1711), were grown in monolayers cultures using SF-900 medium (GIBCO BRL). Antisera and monoclonal anti-Met antibodies were raised against a synthetic peptide corresponding to the nineteen C-terminal amino acids of the human MET sequence (Prat, M., et al., Mol. Cell. Biol. 11 (12): 5954–5962 (1991)) . Antibodies against p85 are described by Otsu et al. (Otsu, M., et al., Cell 65: 91–104 (1991)).

The synthetic phosphopeptides were synthesized with the procedure described in Example 1 to 3.

Expression of HGF/SF receptor and p85 cDNAs in insect cells using baculoviruses vectors. Recombinant HGF/SF receptor and p85 baculoviruses were constructed as previously described (Bardelli, A., et al., Oncogene 7: 1973–1978 (1992); Otsu, M., et al., Cell 65: 91–104 (1991)) and used to infect Sf9 cells (Piwnica-Worms, H. et al., J. Virol. 64: 61–6 (1990)). GST-SH2 domain fusion proteins. The N- and C-SH2 domains of the bovine PI 3-kinase p85 subunit (amino acids 314–431 and 612–722) were obtained by polymerase chain reaction and cloned into the pGEX-2 bacterial expression vector (Smith, D. B., and Johnson K. S., Gene 67: 31–40 (1988). Glutathione-S-transferase (GST)-SH2 fusion proteins were purified from bacterial lysates by glutathione affinity chromatography (Panayotou, G., et al. EMBO J., 11: 4261–4272 (1992)). Amino acid analysis on an Applied Biosystems 420A analyzer was used to determine the concentration of the recombinant proteins.

Site-directed mutagenesis and expression in COS 7 cells of the MET cDNA. The cloning of the MET cDNA has been reported previously (Ponzetto, C., et al., Oncogene 6: 553–559 (1991), EMBL Data-Bank reference n° X54559). The 3' end fragment from nucleotide 2355 to the end was subcloned in pSELECT™-1. Site-directed mutagenesis was performed using an in vitro oligonucleotide site-directed mutagenesis system (Altered Sites™ in vitro Mutagenesis System, Promega). Oligonucleotides were synthesized using an Applied Biosystem 391 apparatus. Mutant clones were identified by sequencing (T7 sequencing kit from Pharmacia). Full size MET cDNAs carrying the appropriate Tyr-Phe mutation were reconstructed in the PMT2 vector which contains the major late Adenovirus promoter. All plasmids were transfected by lipofectin (GIBCO BRL) in COS 7 cells.

In vitro association experiments. Sf9 cells expressing the recombinant HGF/SF receptor (approximately 4×10$^6$ cells/point) were lysed 36 hours after infection in buffer A (10 mM Tris-HCl buffer pH 7.5, 10% glycerol, 1% Triton X-100, 150 mM NaCl, 5 mM EDTA), supplemented with 0.2 mM phenyl-methylsulfonyl fluoride, 1 µg/ml leupeptin, 0.1 TIU/ml aprotinin and 1 µg/ml pepstatin. Lysates were clarified at 15,000×g at 4° C. for 15 minutes and the supernatants immunoprecipitated after 2 hours incubation with anti-Met antibodies coupled to Protein A-Sepharose. Immunocomplexes were washed three times with buffer A, once with buffer B (10 mM Tris-HCl pH 7.4, 100 mM NaCl, 1 mM EDTA) and once with buffer C (25 mM 4-(2-hydroxyethyl)-1-piperazine-ethanesulfonic acid (HEPES) buffer pH 7.2, 100 mM NaCl, 5 mM $MgCl_2$). Samples were pre-phosphorylated by incubation for 15 minutes at 25° C. in buffer C with 10 µM unlabelled ATP and then washed three times with cold buffer A supplemented with 1 mM sodium ortho-vanadate. Association between the immobilized receptor and the baculovirus-expressed p85 was carried out as previously described (Bardelli, A., et al., Oncogene 7: 1973–1978 (1992)). For the association experiments with the PI 3-kinase holoenzyme three days serum-starved A549 cells (approx. 2×10$^6$ cells/point) were used as a source of PI 3-kinase. A549 cells were Dounce-homogenized in MOPS buffer (20 mM 3-(N-morpholino)propanesulfonic acid) (pH 7.5), 1 mM $MgCl_2$, 0.1 mM EDTA, 200 mM sucrose, 1 mM sodium ortho-vanadate), supplemented with 0.2 mM phenylmethylsulfonyl fluoride, 1 µg/ml leupeptin, 0.1 TIU/ml aprotinin and 1 µg/ml pepstatin. Homogenates were centrifuged at 100,000×g for 20 minutes at 4° C. When checking for the ability of phosphopeptides to block the association with the receptor, cell lysates were pre-incubated with the phosphopeptides for 1 hour at 4° C. prior to incubation with the immobilized recombinant HGF/SF receptor. Following association, immunocomplexes were washed three times with buffer A, twice with buffer D (0.5M LiCl, 100 mM Tris-HCl pH 7.6), and twice with buffer B.

The presence of the p85 subunit of the PI 3-kinase in the receptor immunoprecipitate was determined by: i) labelling of the receptor and associated proteins with [γ-$^{32}$P]ATP by in vitro kinase assay; ii) Western immunoblotting; iii) PI 3-kinase activity assay.

In vivo association experiments. Transfected COS 7 cells expressing HGF/SF receptor mutants were stimulated for 10 minutes at 37° C. with HGF/SF (12 ng/ml) and lysed in buffer A in the presence of 1 mM sodium ortho-vanadate. Lysates were clarified at 15,000×g at 4° C. for 15 minutes and the supernatants immunoprecipitated after 2 hours incubation with anti-Met antibodies specific for the human protein coupled to Protein A-Sepharose. Complexes were washed twice with buffer A, twice with buffer D, and twice with buffer B. The presence of the receptor-associated PI 3-kinase in the complex was determined by PI 3-kinase assay as described by Whitman et al. (Whitman, M., et al., Nature 315: 239–242 (1985)).

In vitro kinase assay. Receptor-associated proteins were labelled in 20 μl of buffer C, in the presence of 10 μCi [γ-$^{32}$P]ATP (specific activity 7,000 Ci/Mm; Amersham) at 25° C. for 15 minutes. The reaction was stopped by adding 1 ml of ice-cold Buffer A without protease inhibitors. Samples were washed three times with cold buffer A. The labelled immunocomplexes were eluted from Protein A-Sepharose in boiling Laemmli buffer. Supernatants were then subjected to 8% sodium dodecyl-sulfate polyacrylamide gel electrophoresis (SDS-PAGE).

Western immunoblotting. Immunoprecipitates after the association were solubilized in boiling Laemmli buffer, separated on 8% SDS-PAGE and electro-transferred into nitrocellulose filters (Hi-bond, Amersham). Filters were then incubated with the indicated antibodies and specific binding was detected by the enhanced chemiluminescence system (ELC™, Amersham).

Tryptic phosphopeptide mapping. $^{32}$P-labelled bands corresponding to in vitro-phosphorylated wild type and mutant HGF/SF receptors were excised from polyacrylamide gels and treated as previously described (Ferracini, R., et al., J. Biol. Chem. 266: 19558–19564 (1991)). Tryptic peptide digests were dissolved in 100% dimethylformamide, diluted to 50% with the HPLC loading buffer (0.1% trifluoroacetic acid in water) and separated by high performance liquid chromatography (HPLC) on a reverse phase $C_2/C_{18}$ Superpack Pep-S column (Pharmacia) with a gradient of acetonitrile (0–32% in 70 minutes) in the presence of 0.1 trifluoroacetic acid, with a flow of 1 ml/minute. The eluted radioactivity was monitored by a Radiomatic A-100 radioactive flow detector (Packard Instrument Co.). As a control, a synthetic peptide (I24K, neosystem Laboratories), was separated on HPLC as above and analyzed at 214 nm. I24K encompasses 24 amino acids from Isoleucine 1337 to Lysine 1360 of the Met protein sequence, and thus corresponds to the predicted tryptic phosphopeptide of interest, except for the fact that it is not phosphorylated.

Analysis of the interaction of $Y_{1349}$ and $Y_{1356}$ with the p85 N- and C-SH2 domains using the BIAcore. Details of the construction and principle of operation of the BIAcore biosensor have been described (Jonsson, U., et al., Biotechniques 11: 520–527 (1991); Jonsson, U., and M. Malmquist. 1992. In F. Turner (ed), Advances in Biosensor, vol. 2 JAI Press, London (1992); Karlsson, R., et al., J. Immunol. Meth. 145: 229–246 (1991)). The SH2 domains used in these experiments were desalted through a Pharmacia column on a SMART chromatography system in order to achieve buffer exchange to the BIAcore running buffer, consisting of 20 mM Hepes, pH 7.4, 150 mM NaCl, 3.4 mM EDTA, 0.005% Tween 20 and 4 mM DTT. Avidin (Boehringer) at 50 μg/ml in 20 mM sodium acetate buffer, pH 4.0, was immobilized on the sensor chip surface after activation with a 1:1 mixture of N-hydroxysuccinimide (NHS) and N-Ethyl-N'-(3-dimethyl-aminopropyl)-carbodiimide hydrochloride (EDC) (Pharmacia).

Excess reactive groups were blocked with ethanolamine (1.0M). Biotinylated phosphopeptide Y751 (DMSKDES-VDYVPMLDMK) (SEQ. ID NO: 26) was injected over the avidin at a flow rate of 5 μg/sec for 50 seconds. Nonspecifically bound material was removed with a short pulse (4 seconds) of 0.1% SDS.

GTS-SH2 domain fusion proteins were mixed with a range of concentrations of HGF/SF receptor phosphopeptides and injected over the surface at 5 μl/min for 40 seconds at a constant temperature of 25° C. The material bound to the surface was removed with a 4 seconds pulse of 0.1% SDS, which brought the signal to background level.

RESULTS

Competition experiments with synthetic phosphopeptides. In our initial studies we made use of synthetic phosphopeptides to outcompete p85 or PI 3-kinase in in vitro association experiments with the recombinant HGF/SF receptor. The phosphopeptides were designed to cover all the possible tyrosines present in the cytoplasmic portion of the HGF/SF receptor. The list of the phosphopeptides is shown above in the section entitled "Detailed description of the invention". Sixteen phosphopeptides were eight amino acids long and began with a phosphotyrosine residue at the N-terminus. One phosphopeptide was twelve amino acids long and included two phosphotyrosines. Previous work carried out with the PDGF receptor had shown that the four amino acids located immediately downstream to the phosphotyrosine are important for defining the SH2 recognition site (Fantl, W. J., et al., Cell 69: 413–423 (1992)).

In the experiment shown in FIG. 1 we used lysates of insect cells (Sf9) infected with a recombinant baculovirus as a source of p85 protein (Otsu, M., et al., Cell 65: 91–104 (1991)). Such lysates were diluted appropriately (see Materials and Methods) and pre-incubated with each of the phosphopeptides (10 μM) before incubation with the HGF/SF recombinant receptor. The receptor was immunoprecipitated from lysates of Sf9 cells infected with a recombinant baculovirus carrying a full-size human MET cDNA (Bardelli, A., et al. Oncogene 7: 1973–1978 (1992)). In these cells the receptor is synthesized largely in the form of the uncleaved precursor ($MET_{Bac}$ in the Figures) which is, however, fully functional (Bardelli, A., et al. Oncogene 7: 1973–1978 (1992)). The receptor was immobilized on protein-A Sepharose beads, and pre-phosphorylated with cold ATP. After association, the beads were washed and the complexes were phosphorylated with [γ-$^{32}$P]-ATP. During the phosphorylation reaction both the receptor and p85 become labelled, and thus detectable in SDS-PAGE. FIG. 1 shows that only three of the phosphopeptides efficiently outcompeted p85: H-Tyr*-Glu-Val-Met-Leu-Lys-Cys-Trp-OH (SEQ. ID NO: 19), H-Tyr*-Val-His-Val-Asn-Ala-Thr-Tyr-OH (SEQ. ID NO: 20), H-Tyr*-Val-Asn-Val-Lys-Cys-Val-Ala-OH (SEQ. ID NO: 22).

The phosphopeptide H-Tyr*-Val-His-Val-Asn-Ala-Thr-Tyr*-Val-Asn-Val-Lys-OH (SEQ. ID NO: 21) also completely prevented p85 binding, while phosphopeptide H-Tyr*-Cys-Pro-Asp-Pro-Leu-Tyr-Glu-OH (SEQ. ID NO: 18) was only partially effective. In the experiment shown in FIG. 2 we sought to roughly define the relative affinities of these phosphopeptides for p85. The experiment was carried out as the previous one, but the phosphopeptides were used at concentrations varying between 10 nM and 1 µM. The efficiency at outcompeting p85 was highest for H-Tyr*-Glu-Val-Met-Leu-Lys-Cys-Trp-OH (SEQ. ID NO: 19), followed by H-Tyr*-Val-Asn-Val-Lys-Cys-Val-Ala-OH (SEQ. ID NO: 22), H-Tyr*-Val-His-Val-Asn-Ala-Thr-Tyr-OH (SEQ. ID NO: 20), and H-Tyr*-Cys-Pro-Asp-Pro-Leu-Tyr-Glu-OH (SEQ. ID NO: 18).

The phosphopeptide H-Tyr*-Val-His-Val-Asn-Ala-Thr-Tyr*-Val-Asn-Val-Lys-OH (SEQ. ID NO: 21), seemed to be comparable to H-Tyr*-Val-Asn-Val-Lys-Cys-Val-Ala-OH (SEQ. ID NO: 22), in its affinity for p85.

Since the interaction with the p110 catalytic subunit could affect the conformation of p85, these results might not reflect the true properties of the SH2 domains of p85 in the complex. To exclude this possibility we carried out the same kind of competition experiments using lysates of A549 cells as a source of PI 3-kinase holoenzyme. The association between the holoenzyme and the recombinant receptor was visualized measuring the PI 3-kinase activity in the receptor complexes. FIG. 3 shows that the phosphopeptides which had proven capable of outcompeting p85 also interfere with binding of the PI 3-kinase holoenzyme to the HGF/SF receptor. In particular it should be noted that the phosphopeptide including both phosphotyrosine 1349 and 1356 seems to be more efficient at displacing the PI 3-kinase holoenzyme from the HGF/SF receptor than those including just one of these residues.

The results of this first set of experiments suggested the possible existence of a double binding site for PI 3-kinase in the HGF/SF receptor, consisting of the phosphotyrosine pairs 1307–1313 and 1349–1356. That a pair of phosphotyrosine residues may be involved has been shown for the PDGF receptor, where $Tyr_{740}$ and $Tyr_{751}$ are known to form the PI 3-kinase binding site (Fantl, W. J., et al., Cell 69: 413–423 (1992); Kazlauskas, A., et al., Mol. Cell. Biol. 12: 2534–2544 (1992)).

Association of p85 or PI 3-kinase holoenzyme with HGF/SF receptor Tyr-Phe mutants. A series of constructs were made by site-directed mutagenesis of the wild type receptor cDNA according to standard methods well known to the skilled in the art. These constructs were transiently expressed in COS 7 cells, to obtain the corresponding Tyr-Phe receptor mutants $Phe_{1003}$, $Phe_{1307}$, $Phe_{1313}$, $Phe_{1349}$, $Phe_{1356}$, and $Phe_{1365}$.

In addition to single amino acid substitutions, some multiple substitutions were also made. In particular, we produced the two double site mutants necessary to further elucidate the results of the competition experiments: the mutant $Phe_{1307-1313}$ and the mutant $Phe_{1349-1356}$.

FIG. 4 shows the results of an association experiment similar to that represented in FIG. 1, carried out using the same source of p85 (expressing Sf9 cells), and using lysate of transfected COS 7 cells as a source of wild type and mutant HGF/SF receptors. Transfected COS 7 cells express the single-chain receptor precursor as well as the proteolytically processed mature form in a 1:1 ratio. After the association reaction the samples were split in two and processed differently to yield the results shown in panels A and B. In panel A both the receptor and p85 are visualized by means of a kinase assay. This panel shows that the mutant receptors are all active, and are present in comparable amounts. While all the other mutants (and in particular $Phe_{1307-1313}$) still bind and phosphorylate p85, only the double mutant $Phe_{1349-1356}$ does not. In panel B after the association the kinase assay was omitted, the samples were run in SDS-PAGE and transferred to nitrocellulose. The Western blot was then decorated with monoclonal antibodies specific for p85. This experiment confirms that only the mutant $Phe_{1349-1356}$ has lost the ability to bind p85. It should be noted that comparing panels A and B the mutant $Phe_{1356}$, although still capable of binding p85, seems to be defective in phosphorylating it. This suggests that in the complex with this receptor mutant, p85 may not be positioned correctly for efficient phosphorylation.

FIG. 5 shows that similar results can be obtained also in vivo. In this experiment the receptor was immunoprecipitated from lysates of transfected COS 7 cells after HGF/SF stimulation. Lysis and immunoprecipitation were done in the presence of sodium orthovanadate, to prevent receptor dephosphorylation. A PI 3-kinase assay was then carried out on the receptor immunoprecipitates, equalized for Met protein content, to quantify the amount of endogenous PI 3-kinase co-precipitated in complex with the receptor. Only the $Phe_{1349-1356}$ double mutant co-precipitated with an amount of PI 3-kinase activity lower than that associated to the wild type receptor. The residual activity bound to the $Phe_{1349-1356}$ double mutant is probably due to the formation of receptor dimers with the endogenous Met protein from COS 7 cells. This interpretation is supported by the fact that the same amount of residual binding is also present on immunoprecipitates obtained from COS 7 cells transfected with a kinase-inactive mutant (TK⁻, FIG. 5).

The results of this second set of experiments indicate that residues $Y_{1349}$ and $Y_{1356}$ mediate binding of PI 3-kinase to the HGF/SF receptor, while residues $Y_{1307}$ and $Y_{1313}$ do not.

Phosphopeptide mapping of wild type and mutant receptors. The results obtained using the mutant receptors imply that tyrosines 1349 and 1356 are phosphorylated in vivo. A synthetic peptide (I24K) was constructed to correspond to the tryptic peptide including these two residues. This peptide required a combination of aqueous and organic solvents for best recovery and eluted at a very late time from the HPLC column used for the separation (see panel A of FIG. 6). When the same procedure was used to run a tryptic digest obtained from a wild type receptor that had been phosphorylated in vitro, a peak eluting at a time very close to that of the non-phosphorylated I24K peptide was recovered (FIG. 6, panel B). This novel peak is absent in the double-site mutant (FIG. 6, panel C) and is reduced in the single-site mutants (not shown). All receptors were expressed in COS 7 cells and phosphorylated in vitro prior to tryptic digestion.

These results indicate that tyrosines 1349–1356 are indeed in vitro phosphorylation sites and, in combination with the association experiment shown in FIG. 5, strongly suggest that the same tyrosine residues are also in vivo phosphorylation sites.

Evaluation of the relative affinities of phosphotyrosine 1349 and 1356 for the N- and C-SH2 domains of p85. The presence of two SH2 domains in the p85 molecule and the need to eliminate two phosphotyrosines in the HGF/SF receptor to abolish PI 3-kinase binding, suggest a model in which each SH2 domain interacts with one of the two tyrosines (Kashishian, A., et al., EMBO J. 11: 1373–1382; Kavanaugh, W. M., et al., Mol. Cell. Biol. 12: 3415–3424 (1992)).

It is therefore interesting to measure the relative affinities of the two phosphopeptides for the N- and C-terminal SH2 domains of p85. We initially attempted to do this using biospecific interaction analysis with the BIAcore instrument (Jonsson, U., et al., Biotechniques 11: 520–527 (1991); Jonsson, U., and M., Malmquist. In F. Turner (ed), Advances in Biosensors, vol. 2 JAI Press, London (1992); Karlsson, R., et al., J. Immunol. Meth. 145: 229–246 (1991)). However, the coupling of the phosphopeptides to the matrix either directly or, after biotinylation, by binding to matrix-immobilized avidin, resulted in no significant response. This was presumably due to the fact that the phosphotyrosine in these peptides is at the N-terminus and immobilization perturbs its binding capacity. We therefore did the affinity measurements in an indirect way, by measuring the ability of the phosphopeptides to inhibit the interaction of the SH2 domains with an immobilized phosphopeptide which includes phosphotyrosine 751 ($Y_{751}$) in the human PDGF receptor and has been shown to have a high affinity for the two SH2 domains. The N- and C-SH2 domains of p85 were mixed with a range of concentrations of the Met phosphopeptides and injected over immobilized Y751 phosphopeptide. FIG. 7 shows the results of these measurements, expressed as % inhibition of binding to phosphopeptide Y751. Although it was not possible to derive the absolute affinities for these interactions, comparison of the values at which half-maximal inhibition is observed provided useful information about the relative affinities. A summary of the data is shown in panel C. The highest apparent affinity is displayed by the $Y_{1313}$ phosphopeptide, which contains the canonical YXXM (SEQ. ID NO: 24) motif. The phosphopeptides $Y_{1349}$ and $Y_{1356}$, which include the unconventional binding site YVXV (SEQ. ID NO: 2), also inhibit binding of p85 N- and C-SH2 domains to phosphopeptide Y751, but at higher concentrations. All phosphopeptides, but more evidently $Y_{1313}$, show a higher affinity for the C-SH2 than for the N-SH2. These data are in agreement with those obtained from the experiment shown in FIG. 2, and indicate that, at least in vitro and under our experimental conditions, the novel binding motif Tyr-Val-Xxx-Val (SEQ. ID NO: 29) (YVXV) has an affinity for p85 two orders of magnitude lower than the canonical consensus.

EXAMPLE 5

Transforming activity of TPR-MET tyr-phe mutants Through the experiments described in Example 4, the tyrosine residues in positions 1349 and 1356 of the HGF/SF receptor (encoded by the MET protooncogene) have been identified as docking sites involved in recruiting and activating PI 3-kinase and possibly additional cytoplasmic transducers. If permanently activated, the transducers act as continuos effectors of the mitogenic signal, thus producing the oncogenic transformation of the cell.

In order to demonstrate the importance of the tyrosine residues in position 1349 and 1356 of the BGF/JF receptor in the process leading to oncogenic transformation, we took advantage of the TPR-MET molecule, the permanently activated form of the MET protooncogene (Gonsatti-Haces, et al. Proc. Natl. Acad. Sci. USA 85: 21–25 (1988)), TPR-MET results from a DNA rearrangement between TPR sequences from chromosome 1 and MET sequences from chromosome 7. The TPR-MET product has a constitutive tyrosine kinase activity responsible for transformation of NIH 3T3 fibroblasts.

Through site-directed mutagenesis, we have mutated to phenylalanine in TPR-MET the tyrosine residues corresponding to position 1349 and 1356 in the receptor molecule.

The TPR-MET wild type protooncogene as well as the mutated forms TPR-MET-$Phe_{1349}$, TPR-MET-$Phe_{1356}$ and TPR-MET-$Phe_{1349-1356}$ have been used to perform a Focus Formation Assay. In this assay Fisher Rat fibroblasts were transfected by calcium phosphate with the different TPR-MET constructs cloned in the pXMT2 plasmid (SambrooK, et al. Molecular Cloning. A laboratory manual (Second edition) page 16–22, Cold Spring Harbor Laboratory Press (1989)). Cells were grown in DMEM containing 5% Foetal Calf Serum and loci were counted after 10 days. The results are summarized in the following table and illustrated in FIG. 9.

|  | TPR—MET | TPR—MET* $Phe^{1349}$ | TPR—MET* $Phe^{1356}$ | TPR—MET* $Phe^{1349-1356}$ |
|---|---|---|---|---|
| transforming activity (foci/μg of DNA/$10^5$ cells) | 800 | 600 | 40 | 0 |
| kinase activity | + | + | + | + |

As can be appreciated either from the above table or from FIG. 8 the mutation of the $Tyr_{1349}$ but especially of $Tyr_{1356}$ produces a substantial decrease in the number of the transforming foci.

Moreover, when both the Tyr residues are mutated to Phenylalanine, the transforming activity of TPR-MET is completely abolished.

These data provide a further demonstration of the biological importance of these sites in that intracellular transduction of the mitogenic signal.

The phosphopeptides of the invention which are able to prevent the binding of the intracellular transducers to $Tyr_{1349}$ and $Tyr_{1356}$ of the HGF/SF receptor are therefore potential inhibitors of the oncogenic transformation.

EXAMPLE 6

Materials and Methods

Cell lines. Lung carcinoma A549 cells and COS-1 cells were routinely cultured in RPMI medium supplemented with 10% FCS. The PA317 amphotropic virus packaging cell line (Miller and Buttimore (1986) Mol. Cell. Biol. 6: 2895–2902) and the ecotropic virus packaging cell line Psi-2 (Mann et al (1983) Cell 33: 153–159) were maintained in Dulbecco's modified Eagle's medium supplemented with 10% FCS.

Monoclonal antibodies and polyclonal antisera. Anti-Shc polyclonal antisera were produced by immunizing rabbits with Shc SH2 domain expressed in bacteria. Anti-TAG serum was produced against a PML peptide (Pandolfi et al., Oncogene 6: 1285–1292 (1991)). Monoclonal antibodies to phosphotyrosine were purchased from Upstate Biotechnology. Anti-Met antibodies were raised against a synthetic peptide corresponding to the 19 C-terminal aminoacids of the human Met protein (Data Bank reference no. X54559).

Immunoprecipitation and western blotting procedures. Lysates were prepared from serum starved and SF/HGF treated A549 cells. Cells were lysed on ice in PY buffer (20 mM Tris HCl pH 7.8, 50 mM NaCl, 50 mM NaF, 30 mM $Na_4P_2O_7$, 5 mM EGTA, 1 mM sodium orthovanadate, 1% vol/vol Triton X-100) containing freshly added protease inhibitors (1 mM phenylmethyl sulphonyl fluoride, 10 mg/ml leupeptin and 5 mg/ml aprotinin). Lysates were clarified by centrifugation at 4° C. and protein concentration determined by BCA reagent (Pierce). For immunoprecipitation experiments, appropriate antibodies were adsorbed on Protein A Sepharose (Pharmacia) and then incubated with cell lysates for 1.5 hrs. at 4° C. Immune complexes were washed 3 times with ice cold NET buffer (50 mM Tris HCl pH 7.5, 150 mM NaCl, 0.1% NP-40, 1 mM EDTA pH 8.0, 0.25% gelatin), eluted and denatured by heating for 3 min. at 95° C. in reducing Laemmli buffer; proteins were then resolved on sodium dodecyl sulfate polyacrylamide gel electrophoresis (SDS-PAGE). For immunoblot analysis, either specific immunoprecipitates or 20–50 mg total cell lysates were transferred onto nitrocellulose filters after SDS-PAGE. After blocking nonspecific reactivity with 2% nonfat dry milk dissolved in TBST (20 mM Tris-HCl pH 7.8, 150 mM NaCl 0.02% Tween 20) (1 hr incubation at 22° C.), filters were probed for 2 hrs at 22° C. with specific antibodies diluted in TBST. After extensive washing, immune complexes were detected with horseradish-peroxidase conjugated species-specific secondary antiserum (Bio Rad) followed by the enhanced chemiluminescence reaction (ECL™, Amersham).

cDNA site-directed mutagenesis and expression. The cloning of the MET cDNA has been reported previously (Ponzetto et al., Oncogene 6: 553–559 (1991)), EMBL Data-Bank reference no. X54559). The 3' end fragment from nucleotide 2355 to the end was subcloned in pSELECT™-1. Site-directed mutagenesis was performed using an in vitro oligonucleotide site-directed mutagenesis system (Altered Sites™ in vitro Mutagenesis System, Promega). Oligonucleotides were synthesized using an Applied Biosystem 391 apparatus. Mutant clones were identified by sequencing (T7 sequencing kit from Pharmacia). Full size MET cDNAs carrying the appropriate Tyr→Phe mutation were reconstructed in the PMT2 vector which contains the major late Adenovirus promoter. All plasmids were transfected by lipofectin (GIBCO BRL) in COS 1 cells. The Shc cDNA carrying the mutation $Y^{317} \rightarrow F$ was cloned into the mammalian expression vector LXSN. The mutated cDNA was tagged with a foreign epitope by in-frame fusion with a 162 bp fragment of the PML cDNA (Pandolfi et al., ibid). The tagged cDNA encodes PML-tagged Shc proteins of 53 and 58 kDa as a result of alternative initiation usage. Detailed description of this construct will be reported elsewhere (Salcini et al., in preparation). The expression vector was cotransfected with a neomycin resistance gene in A549 cells by calcium phosphate. Stable cell lines expressing the tagged Shc proteins were selected by G418.

In vitro binding studies using GST-fusion protein. The region of the Grb2 cDNA corresponding to its SH2 domain (from nucleotide position 256 to nucleotide position 551) was isolated using polymerase chain reaction (PCR) and cloned into the BamHI-EcoRI sites of the bacterial expression plasmid pGEX-2T (GST-Grb2). Cultures of bacteria expressing GST, GST-Grb2 or GST-Shc (Segatto et al., Oncogene 2105–2112 (1993)) were grown for 3–4 hours at 37° C. in LB medium containing 1 mM IPTG. Bacteria were centrifuged, resuspended in 1/100 volume of ice-cold PY buffer, without Triton™ and lysed by sonication. After adding Triton X-100 to 1%, lysates were clarified by centrifugation. Recombinant proteins were purified onto glutathione Sepharose™ (Pharmacia) and used as such for binding assays. For each reaction, about 5 µg of GST, GST-Grb2 or GST-Shc bound to glutathione Sepharose was incubated for 2 hrs. at 4° C. with 300 mg of appropriate cell lysate made in PY buffer. Protein complexes were washed 5 times in ice cold PY buffer, eluted and denatured by heating at 95° C. for 3 min in Laemmli buffer, resolved on SDS-PAGE and analyzed by immunoblot.

Overexpression of Shc proteins. The LSHCSN plasmid was constructed by cloning the Shc coding sequence (Pelicci et al Cell 70: 93–104 (1992)) in the EcoRI restriction site of the LXSN retrovirus plasmid (Miller et al., (1989); gifted from D. Miller). LXSN or LSHCSN plasmids were transfected into the Y2 of PA317 retrovirus packaging cell lines by the calcium phosphate precipitation procedure (Sambrook et al. Molecular Cloning: A Laboratory Manual, 2nd Ed., Cold Spring Harbor Laboratory, Cold Spring Harbour, N.Y. (1989)). After 48 hours, the Y-2 supernatants were used to infect PA317. The cells were then selected with G418 containing medium under limiting dilution conditions. One virus-producing clone was selected, based on high levels of exogenous Shc expression and vital titer and used to infect target cells.

BIAcore analysis.

The basic principles of operation as well as the methodology for obtaining kinetic measurements of SH2 domain interactions using the BIAcore instrument (Pharmacia) have been previously described in detail (Panayotou et al., Mol. Cell. Biol. 13: 3567–3576 (1993), Ponzetto et al., Mol. Cell. Biol. 13: 4600–4608 (1993)). Purified GST-SH2 domains or intact proteins were desalted in BIAcore running buffer (20 mM Hepes, pH 7.4, 150 mM NaCl, 3.4 mM EDTA, 0.005% Tween 20 and 4 mM DTT) and injected over avidin-immobilized, biotinylated phosphopeptides. The amount of phosphopeptides immobilized was normalized by measuring the binding of anti-phosphotyrosine antibodies. Association was measured over a range of protein concentrations and dissociation of bound material was allowed to occur either in buffer flow or upon injection of 20 µM competing, non-biotinylated phosphopetide. Peptide and protein concentrations were calculated by amino acid analysis on an Applied Biosystem amino acid analyzer.

Assay for cell growth and motility. $2.5 \times 10^3$ cells were plated in 96-well plates (Costar) in DMEM medium containing 10% FCS (Flow). After 24 hours the medium was removed and replaced with DMEM containing 5% FCS with a wide range of SF/HGF concentrations (1–10 ng/ml). Cell number was estimated after staining with crystal violet by a colorimetric assay (Kueng et al., Anal. Biochem. 182: 16–19 (1989)); the wells were read at 595 nm in a Microplate Reader (Model 3550, Bio-Rad). Blind-well boyden chambers and polyvinylpyrrolidone-free polycarbonate filters (13 mm 8 µm pores) used for chemotaxis studies were purchased from Nucleopore. Chemotaxis assays were performed as previously described (Albini et al., Cancer Research 47: 3239–3245 (1987)). Cells were labelled with 5-[$^{125}$I]iodo-2'-deoxyuridine (3 µCi/ml 1 n RPMI 1640 medium plus 10% FCS). After 16–20 hr of incubation, cells were trypsinized and washed three times with FCS free medium. $3 \times 10^5$ cells resuspended in the FCS free medium were plated in the upper part of Boyden chambers; in the lower chambers, FCS free medium with or without SF/HGF (5–40 U/ml) was added. Boyden chambers were incubated for 6 hr at 37° C. in a 5% $CO_2$-water saturated atmosphere. Cells attached to the upper side of the filters were mechanically removed after incubation, while the filters with cells migrated to the lower side were fixed and counted in a γ-counter.

RESULTS

Shc proteins bind the tyrosine phosphorylated SF/HGF receptor via the SH2 domain.

Lung carcinoma A549 cells express functional SF/HGF receptors and the three Shc isoforms of 46, 52 and 66 kDa. To test if the tyrosine phosphorylated SF/HGF receptor and Shc form a stable complex in vivo, lysates form SF/HGF-treated cells were immunoprecipitated with anti-Met and immunoblotted with anti-Shc antibodies. Shc proteins co-precipitated with the SF/HGF receptor (FIG. 1A). Similar results were obtained in mirror experiments, where anti-Shc immunoprecipitates from lysates of SF/HGF-treated A549 cells were probed with anti-receptor (anti-Met) antibodies. Shc proteins co-precipitated with the SF/HGF receptor (FIG. 1B). These results demonstrate that SF/HGF receptor and Shc are associated in SF/HGF-stimulated cells.

To further prove that the association between SF/HGF receptor and Shc proteins is strictly dependent on receptor tyrosine phosphorylation, similar experiments were performed using COS-1 cells lysates transiently expressing the cDNAs of either wild-type SF/HGF receptor or of a kinase-defective receptor mutant ($Lys^{1110} \rightarrow A$). As previously described (Longati et al, in press), the wild-type receptor overexpressed in COS-1 cells is constitutively phosphorylated in vivo, while the kinase-inactive $Lys^{1110} \rightarrow A$ mutant is not phosphorylated (FIGS. 2A and B). Stable complexes between the transfected receptor and the endogenous Shc occurred only in COS-1 cells expressing wild-type tyrosine-phosphorylated receptors (FIG. 2C). The Shc-SF/HGF receptor interaction was also explored by reconstituting the complex in vitro using the Shc SH2 domain, expressed in bacteria as a GST-fusion protein. The immobilized Shc-SH2 domain formed a stable association with the tyrosine-phosphorylated receptor solubilized from SF/HGF treated A549 cells, but not with the unphosphorylated receptor solubilized from control cells (FIG. 3A). Binding assays carried out with control GST protein were negative. These results indicate that the SH2 domain of Shc is sufficient for binding to the autophosphorylated SF/HGF receptor in vitro.

Shc proteins bind to phosphotyrosines $Y^{1349}$ and $Y^{1356}$ of the SF/HGF receptor tail.

By phosphopeptide mapping of wild-type and mutant SF/HGF receptor, it has been shown that two residues located in the C-terminal tail of the receptor ($Y^{1349}$ and $Y^{1356}$) are phosphorylated in response to ligand binding (Ponzetto et al., 1993 (ibid)). The possible involvement of these sites in mediating the interaction with Shc was studied by association experiments with receptor mutants where either one or both these tyrosines were mutated to phenylalanine ($Y^{1349} \rightarrow F$, $Y^{1356} \rightarrow F$ or $Y^{1349,1356} \rightarrow F$). As previously shown, receptor molecules carrying individual or combined mutations at these sites are endowed with native tyrosine kinase activity (Ponzetto et al., 1993 (ibid)). COS-1 cells were transfected with constructs expressing the receptor mutants and immunoprecipitated with anti Shc antibodies; immunoprecipitates were blotted with anti-Met receptor antibodies. The ability of the single mutant receptors $Y^{1349} \rightarrow F$ or the $Y^{1356} \rightarrow F$ to associate with endogenous Shc was only slightly lower than that of the wild type receptor or that of a control receptor carrying an irrelevant ($Y^{1003} \rightarrow F$) mutation. Conversely, the $Y^{1349,1356} \rightarrow F$ double mutant completely lost its ability to bind Shc proteins (FIG. 4).

The direct interaction between the SH2 domain of Shc and phosphotyrosine $Y^{1349}$ or $Y^{1356}$ was confirmed by real-time Biosensor analysis (Panayotou et al., ibid; Felder et al., Mol. Cell. Biol. 13: 1449–1455 (1993)) The synthetic phosphopetide VNATY$^{1356*}$VNVK, derived from the receptor tail sequence, was specifically bound by the affinity-purified GST-SH2 domain of Shc (FIG. 5). Similar results were obtained with the peptide IGEHY$^{1349*}$VHVN. In both cases, the affinity constant, calculated from the ratio between the dissociation rate ($K_{diss}$) and the association rate constants ($K_{ass}$), was too high to be exactly determined.

These data show that Shc binds with low affinity to either tyrosine 1349 or tyrosine 1356 of the SF/HGF receptor tail.

Overexpression of Shc proteins increases the motogenic response to SF/HGF. SF/HGF is motogenic for epithelial cells that, after stimulation, migrate through the filters of blind-well Boyden chambers (Giordano et al., Proc. Natl. Acad. Sci. USA 90: 649–653 (1993)). The effect of Shc on the motogenic response was investigated by overexpressing the protein in A549 cells. Cells were infected with an amphotropic retrovirus carrying the Shc cDNA and a number of different infected bulk cell populations were chosen for their high levels of Shc expression, according to western blot analysis with anti-Shc antibodies.

The motogenic response of A549 cells overexpressing Shc proteins was significantly higher than that elicited in control uninfected cells or in cells infected with the vector alone (FIG. 6, lower panel). Higher responses to SF/HGF by cells overexpressing Shc were observed at all ligand concentrations tested (FIG. 6, upper panel).

The mitogenic response was measured either by cell count or by thymidine incorporation. Shc overexpression in A549 cells had no effect on cell growth in response either to SF/HGF or to serum. Similarly, the SF/HGF-induced guanine nucleotide exchanger activity on Ras, measured as previously described (Graziani et al., J. Biol. Chem. 268: 9165–9168 (1993)), was not significantly affected by overexpression of exogenous Shc.

Shc proteins are phosphorylated on $Y^{317}$ after binding to the SF/HGF receptor.

To determine if Shc is phosphorylated in response to the activation of SF/HGF receptor kinase A549 cells were stimulated with recombinant SF/HGF, lysed, immunoprecipitated with anti-Shc and immunoblotted with anti-phosphotyrosine antibodies. A marked increase in tyrosine-phosphorylation of p46$^{Shc}$, p52$^{Shc}$ and p66$^{Shc}$ was detectable in A549 cells after 5 min. stimulation (FIG. 1C), indicating that Shc is a substrate of the SF/HGF receptor. Similar experiments were performed in COS-1 cells transfected with the SF/HGF receptor. In cells overexpressing the wild-type (constitutively active) receptor kinase, endogenous Shc proteins were tyrosine phosphorylated. However, Shc was not phosphorylated in COS-1 cells transfected with the $Lys^{1110} \rightarrow A$ kinase negative receptor (FIG. 2D).

By phosphopeptide mapping and mutation analysis it has been shown that the major phosphorylation site of Shc in EGF-treated cells is $Y^{317}$ (Salcini et al., in preparation). To ascertain that the same residue is also phosphorylated after SF/HGF treatment, a tagged SHC cDNA with a $Y^{317} \rightarrow F$ mutation was expressed into A549 cells. In these cells, after SF/HGF treatment, the $Y^{317} \rightarrow F$ mutant, selectively immunoprecipitated by anti-"tag" antibodies was not phosphorylated on tyrosine (FIG. 1D).

Shc proteins phosphorylated on $Y^{317}$ form specific complexes with the Grb2 "adaptor".

The possibility that SF/HGF triggers formation of a Shc-Grb2 complex in A549 cells following SF/HGF stimulation was tested by probing Western blots of anti-Shc immunoprecipitates with anti-Grb2 antibodies. As shown in FIG. 1E, the Shc protein phosphorylated in response to SF/HGF is associated with Grb2. This association is mediated via the SH2 domain of Grb2, as shown by in vitro experiments using immobilized SH2 domain of Grb2 (expressed in bacteria as GST fusion protein) and cytoplasmic lysates prepared from control or SF/HGF-stimulated A549 cells. The amount of Shc bound by the Grb2 fusion protein increases significantly after SF/HGF stimulation (FIG. 3B).

Figure 7B:
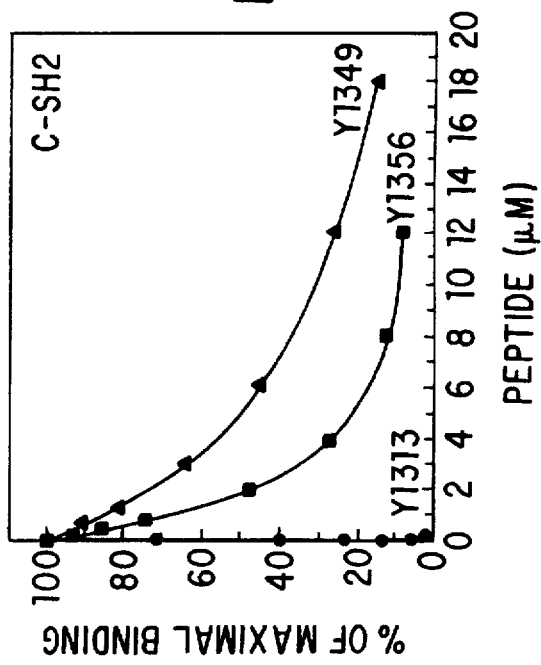
Figure 7C:
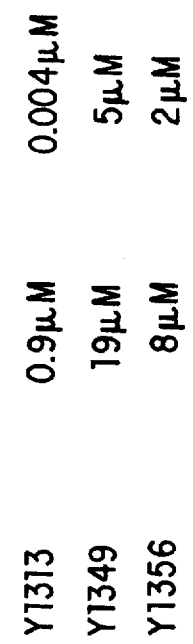

Kinetic parameters and equilibrium dissociation constants or this interaction were derived using a biosensor to measure in real-time binding of the Grb2 GST-SH2 fusion protein with the immobilized tyrosine-phosphorylated Shc peptide DDPSY$^{317*}$VNVQ (SEQ. ID NO: 27) (FIG. 7). The data obtained were used to calculate the $K_{ass}$(2.6×10$^5$ M$^{-1}$s$^{-1}$) as shown in FIG. 7C. The $K_{diss}$ was measured both in buffer and in the presence of competing phosphopeptide to prevent rebinding. As shown in FIG. 7B, addition of the competing phosphopeptide had a dramatic effect on dissociation rate, as previously observed for other SH2 domain-phosphopeptide interactions (Panayotou et al., 1993 (ibid); Felder et al., 1993 (ibid)). The value of the $K_{diss}$ obtained was 0.04 S$^{-1}$, giving an overall affinity of 153 nM.

These data show that phosphorylation of Shc proteins on tyrosine Y$^{317}$ in response to SF/HGF determine the formation of high affinity docking site for the Grb2 "adaptor". Phosphorylated Shc proteins may thus function as bridging molecules between the activated SF/HGF receptor and Grb2. Interestingly, the amino acid sequence of the Shc docking site for Grb2, Y$^{317}$VNV (SEQ. ID NO: 3), is identical to the sequence located in the SF/HGF receptor tail (FIG. 8), Y$^{1356}$VNV (SEQ. ID NO: 3), is identical to the sequence located in the SF/HGF receptor tail (FIG. 8), Y$^{1356}$VNV (SEQ. ID NO: 3), which has been shown to directly bind Grb2 upon ligand stimulation (Ponzetto et al., submitted).

The Shc proteins do not form concatamers

The Shc sequence Y$^{317}$VNV (SEQ. ID NO: 3) is identical to one of the two Shc binding sites present in the SF/HGF receptor (FIG. 8). This observation suggests that Shc may form concatamers by binding phosphotyrosine Y$^{317}$ of another Shc molecule. The biosensor was used to compare binding of the Shc SH2 domain to the phosphopeptide DDPS<u>Y$^{317}$VNVQ</u> (SEQ. ID NO: 27), present on the Shc molecule, and to the phosphopeptide VNAT<u>Y$^{317}$VNVK</u> (SEQ. ID NO: 28), present on the SF/HGF receptor. Shc-SH2 bound much more weakly to the Shc-derived phosphopeptide than to the SF/HGF receptor-derived phosphopeptide (FIG. 5). These data indicate that amino acids at the N-terminal of Y$^{317}$ (in Shc) and of Y$^{1356}$ (in SF/HGF receptor) are recognized by the SH2 domain of Shc. Thus Shc-Shc association is not favoured in vivo, and the Shc phosphotyrosine residue Y$^{317}$ is available to bind other molecules, rather than to mediate the formation of concatamers.

CONCLUSIONS

In conclusion, a peptide having a length of e.g. 4 to 20 amino acids encompassing the docking site of Shc (Y$^{317}$VNV) (SEQ. ID NO: 3), particularly the peptide H-Asp-Asp-Pro-Ser-Tyr-Val-Asn-Val-Gln-OH (SEQ. ID NO: 27) (DDPSY*VNVQ) and a peptide having a length of e.g. 4 to 20 amino acids encompassing the Tyr$^{1356}$ recognition motif of the hepatocyte growth factor receptor (Y$^{1356}$VNV) (SEQ. ID NO: 3), particularly the peptide H-Val-Asn-Ala-Thr-Tyr*-Val-Asn-Val-Lys-OH (SEQ. ID NO: 28) (VNATY*VNVK), wherein Tyr* (Y*) represents a phosphorylated or unphosphorylated tyrosine residue, are able to bind Grb2-SH2 domain. Thus, they are useful to compete for and to prevent association of the SH2 of Grb2 protein with tyrosine phosphorylated receptors such as activated hepatocyte growth factor receptor (HSF/SF receptor), PDGF receptor, EGF receptor or with other cytosolic tyrosine phosphorylated transducers such as Shc or IRS-1 protein, preventing mitogenesis and hence tumoral proliferation.

On the other hand, peptides encompassing the Tyr$^{1356}$ or the Tyr$^{1349}$ recognition motif of the hepatocyte growth factor receptor (Y$^{1356}$VNV or Y$^{1349}$VHV respectively) (SEQ. ID NOS: 3 and 4), particularly the above mentioned peptide H-Val-Asn-Thr-Tyr*-Val-Asn-Val-Lys-OH (SEQ. ID NO: 28) (VNATY*VNVK) and the peptide H-Ile-Gly-Glu-His-Tyr*-Val-His-Val-Asn-OH (SEQ. ID NO: 30) (IGEHY*VHVN), or a peptide containing both the above mentioned tyrosine residues such as H-Ile-Gly-Glu-His-Tyr*-Val-His-Val-Asn-Ala-Thr-Tyr*-Val-Asn-Val-Lys-OH (SEQ. ID NO: 31) (IGEHY*HVNATY*VNVK) wherein Tyr* (Y*) represents phosphorylated or unphosphorylated tyrosine residue, are able to bind Shc-SH2 domain. Thus, they are useful to compete for and to prevent the SH2 association of Shc protein with tyrosine phosphorylated receptors such as activated hepatocyte growth factor receptor, EGF receptors or with other cytosolic tyrosine phosphorylated transducers like IRS-1 or cytosolic tyrosine kinases such as Src, preventing mitogenesis and particularly motogenesis and hence preventing spreading of tumour cells. Thus, the peptides exert antitumoral and antimetastatic actions.

As mentioned above, the peptide of the invention may be advantageously administered in unphosphorylated form as a pro-drug; in this case the peptide may be biochemically transformed into its phosphorylated form inside the cell where it exerts its pharmacological action.

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 4 amino acids (B) TYPE: amino acid
                (D) TOPOLOGY: unknown (ii) MOLECULE TYPE: peptide (xi) SEQUENCE DESCRIPTION: SEQ ID NO:1:

Tyr  Met  Xaa  Met
        1

(2) INFORMATION FOR SEQ ID NO:2:

(i) SEQUENCE CHARACTERISTICS:
                (A) LENGTH: 4 amino acids
                (B) TYPE: amino acid
                (D) TOPOLOGY: unknown (ii) MOLECULE TYPE: peptide (xi) SEQUENCE DESCRIPTION: SEQ ID NO:2:

Tyr  Val  Xaa  Met
        1

(2) INFORMATION FOR SEQ ID NO:3:

(i) SEQUENCE CHARACTERISTICS:
                (A) LENGTH: 4 amino acids
                (B) TYPE: amino acid
                (D) TOPOLOGY: unknown (ii) MOLECULE TYPE: peptide (xi) SEQUENCE DESCRIPTION: SEQ ID NO:3:

Tyr  Val  Asn  Val
        1

(2) INFORMATION FOR SEQ ID NO:4:

(i) SEQUENCE CHARACTERISTICS:
                (A) LENGTH: 4 amino acids
                (B) TYPE: amino acid
                (D) TOPOLOGY: unknown (ii) MOLECULE TYPE: peptide (xi) SEQUENCE DESCRIPTION: SEQ ID NO:4:

Tyr  Val  His  Val
        1

(2) INFORMATION FOR SEQ ID NO:5:

(i) SEQUENCE CHARACTERISTICS:
                (A) LENGTH: 6 amino acids
                (B) TYPE: amino acid
                (D) TOPOLOGY: unknown (ii) MOLECULE TYPE: peptide (ix) FEATURE:
                (A) NAME/KEY: Modified-site
                (B) LOCATION: 1
                (D) OTHER INFORMATION: /note= "At position 1, Xaa may be
                        from 0-16 amino acids and the total length of the
                        peptide may be from 4-20 amino acids."

(ix) FEATURE:
                (A) NAME/KEY: Modified-site
                (B) LOCATION: 6
                (D) OTHER INFORMATION: /note= "At position 6, Xaa may be
                        from 0-16 amino acids and the total length of the
                        peptide may be from 4-20 amino acids."

(xi) SEQUENCE DESCRIPTION: SEQ ID NO:5:

```
Xaa  Tyr  Val  Asn  Val  Xaa
1                    5
```

( 2 ) INFORMATION FOR SEQ ID NO:6:

( i ) SEQUENCE CHARACTERISTICS:
            ( A ) LENGTH: 6 amino acids
            ( B ) TYPE: amino acid
            ( D ) TOPOLOGY: unknown ( i i ) MOLECULE TYPE: peptide ( i x ) FEATURE:
            ( A ) NAME/KEY: Modified-site
            ( B ) LOCATION: 1
            ( D ) OTHER INFORMATION: /note= "At position 1, Xaa may be
                  from 0 to 16 amino acids and the length of the
                  peptide may be from 4-20 amino acids."

( i x ) FEATURE:
            ( A ) NAME/KEY: Modified-site
            ( B ) LOCATION: 6
            ( D ) OTHER INFORMATION: /note= "At position 6, Xaa may be
                  from 0-16 amino acids and the total length of the
                  peptide may be from 4-20 amino acids. "

( x i ) SEQUENCE DESCRIPTION: SEQ ID NO:6:

```
Xaa  Tyr  Val  His  Val  Xaa
1                    5
```

( 2 ) INFORMATION FOR SEQ ID NO:7:

( i ) SEQUENCE CHARACTERISTICS:
            ( A ) LENGTH: 8 amino acids
            ( B ) TYPE: amino acid
            ( D ) TOPOLOGY: unknown ( i i ) MOLECULE TYPE: peptide ( i x ) FEATURE:
            ( A ) NAME/KEY: Modified-site
            ( B ) LOCATION: 1
            ( D ) OTHER INFORMATION: /note= "The Tyr residue at position 1
                  may be phosphorylated.

( x i ) SEQUENCE DESCRIPTION: SEQ ID NO:7:

```
Tyr  Asp  Ala  Arg  Val  His  Thr  Pro
1                    5
```

( 2 ) INFORMATION FOR SEQ ID NO:8:

( i ) SEQUENCE CHARACTERISTICS:
            ( A ) LENGTH: 8 amino acids
            ( B ) TYPE: amino acid
            ( D ) TOPOLOGY: unknown ( i i ) MOLECULE TYPE: peptide ( i x ) FEATURE:
            ( A ) NAME/KEY: Modified-site
            ( B ) LOCATION: 1
            ( D ) OTHER INFORMATION: /note= "The Tyr residue at position 1
                  may be phosphorylated.

( x i ) SEQUENCE DESCRIPTION: SEQ ID NO:8:

```
Tyr  Arg  Ala  Thr  Phe  Pro  Glu  Asp
1                    5
```

( 2 ) INFORMATION FOR SEQ ID NO:9:

( i ) SEQUENCE CHARACTERISTICS:
            ( A ) LENGTH: 8 amino acids (B) TYPE: amino acid
            (D) TOPOLOGY: unknown (i i) MOLECULE TYPE: peptide (i x) FEATURE:
            (A) NAME/KEY: Modified-site
            (B) LOCATION: 1
            (D) OTHER INFORMATION: /note= "The Tyr residue at position 1
                may be phosphorylated.

(x i) SEQUENCE DESCRIPTION: SEQ ID NO:9:

Tyr Pro Leu Thr Asp Met Ser Pro
1               5

(2) INFORMATION FOR SEQ ID NO:10:

(i) SEQUENCE CHARACTERISTICS:
            (A) LENGTH: 8 amino acids
            (B) TYPE: amino acid
            (D) TOPOLOGY: unknown (i i) MOLECULE TYPE: peptide (i x) FEATURE:
            (A) NAME/KEY: Modified-site
            (B) LOCATION: 1
            (D) OTHER INFORMATION: /note= "The Tyr residue at position 1
                may be phosphorylated.

(x i) SEQUENCE DESCRIPTION: SEQ ID NO:10:

Tyr His Gly Thr Leu Leu Asp Asn
1               5

(2) INFORMATION FOR SEQ ID NO:11:

(i) SEQUENCE CHARACTERISTICS:
            (A) LENGTH: 8 amino acids
            (B) TYPE: amino acid
            (D) TOPOLOGY: unknown (i i) MOLECULE TYPE: peptide (i x) FEATURE:
            (A) NAME/KEY: Modified-site
            (B) LOCATION: 1
            (D) OTHER INFORMATION: /note= "The Tyr residue at position 1
                may be phosphorylated.

(x i) SEQUENCE DESCRIPTION: SEQ ID NO:11:

Tyr Met Lys His Gly Asp Leu Arg
1               5

(2) INFORMATION FOR SEQ ID NO:12:

(i) SEQUENCE CHARACTERISTICS:
            (A) LENGTH: 8 amino acids
            (B) TYPE: amino acid
            (D) TOPOLOGY: unknown (i i) MOLECULE TYPE: peptide (i x) FEATURE:
            (A) NAME/KEY: Modified-site
            (B) LOCATION: 1
            (D) OTHER INFORMATION: /note= "The Tyr residue at position 1
                may be phosphorylated.

(x i) SEQUENCE DESCRIPTION: SEQ ID NO:12:

Tyr Leu Ala Ser Lys Lys Phe Val
1               5

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /note= "The Tyr residue at position 1
            may be phosphorylated.

( x i ) SEQUENCE DESCRIPTION: SEQ ID NO:13:

```
Tyr  Asp  Lys  Glu  Tyr  Tyr  Ser  Val
1                   5
```

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /note= "The Tyr residue at position 1
            may be phosphorylated.

( x i ) SEQUENCE DESCRIPTION: SEQ ID NO:14:

```
Tyr  Tyr  Ser  Val  His  Asn  Lys  Thr
1                   5
```

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /note= "The Tyr residue at position 1
            may be phosphorylated.

( x i ) SEQUENCE DESCRIPTION: SEQ ID NO:15:

```
Tyr  Ser  Val  His  Asn  Lys  Thr  Gly
1                   5
```

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /note= "The Tyr residue at position 1
            may be phosphorylated.

( x i ) SEQUENCE DESCRIPTION: SEQ ID NO:16:

```
Tyr  Pro  Asp  Val  Asn  Thr  Phe  Asp
 1                 5
```

(2) INFORMATION FOR SEQ ID NO:17:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "The Tyr residue at position 1 may be phosphorylated.

(xi) SEQUENCE DESCRIPTION: SEQ ID NO:17:

```
Tyr  Leu  Leu  Gln  Gly  Arg  Arg  Leu
 1                 5
```

(2) INFORMATION FOR SEQ ID NO:18:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "The Tyr residue at position 1 may be phosphorylated.

(xi) SEQUENCE DESCRIPTION: SEQ ID NO:18:

```
Tyr  Cys  Pro  Asp  Pro  Leu  Tyr  Glu
 1                 5
```

(2) INFORMATION FOR SEQ ID NO:19:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "The Tyr residue at position 1 may be phosphorylated.

(xi) SEQUENCE DESCRIPTION: SEQ ID NO:19:

```
Tyr  Glu  Val  Met  Leu  Lys  Cys  Trp
 1                 5
```

(2) INFORMATION FOR SEQ ID NO:20:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /note= "The Tyr residue at position 1 may be phosphorylated.

( x i ) SEQUENCE DESCRIPTION: SEQ ID NO:20:

Tyr Val His Val Asn Ala Thr Tyr
1               5

( 2 ) INFORMATION FOR SEQ ID NO:21:

( i ) SEQUENCE CHARACTERISTICS:
        ( A ) LENGTH: 12 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /note= "The Tyr residue at position 1
            may be phosphorylated.

( i x ) FEATURE:
        ( A ) NAME/KEY: Modified-site
        ( B ) LOCATION: 8
        ( D ) OTHER INFORMATION: /note= "The Tyr residue at position 8
            may be phosphorylated.

( x i ) SEQUENCE DESCRIPTION: SEQ ID NO:21:

Tyr Val His Val Asn Ala Thr Tyr Val Asn Val Lys
1               5                   10

( 2 ) INFORMATION FOR SEQ ID NO:22:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /note= "The Tyr residue at position 1
            may be phosphorylated.

( x i ) SEQUENCE DESCRIPTION: SEQ ID NO:22:

Tyr Val Asn Val Lys Cys Val Ala
1               5

( 2 ) INFORMATION FOR SEQ ID NO:23:

( i ) SEQUENCE CHARACTERISTICS:
        ( A ) LENGTH: 8 amino acids
        ( B ) TYPE: amino acid
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /note= "The Tyr residue at position 1
            may be phosphorylated.

( x i ) SEQUENCE DESCRIPTION: SEQ ID NO:23:

Tyr Pro Ser Leu Leu Ser Ser Glu
1               5

( 2 ) INFORMATION FOR SEQ ID NO:24:

( i ) SEQUENCE CHARACTERISTICS:

(A) LENGTH: 4 amino acids
(B) TYPE: amino acid
(D) TOPOLOGY: unknown (ii) MOLECULE TYPE: peptide (xi) SEQUENCE DESCRIPTION: SEQ ID NO:24:

Tyr Xaa Xaa Met
1

(2) INFORMATION FOR SEQ ID NO:25:

(i) SEQUENCE CHARACTERISTICS:
(A) LENGTH: 4 amino acids
(B) TYPE: amino acid
(D) TOPOLOGY: unknown (ii) MOLECULE TYPE: peptide (xi) SEQUENCE DESCRIPTION: SEQ ID NO:25:

Tyr Glu Val Met
1

(2) INFORMATION FOR SEQ ID NO:26:

(i) SEQUENCE CHARACTERISTICS:
(A) LENGTH: 17 amino acids
(B) TYPE: amino acid
(D) TOPOLOGY: unknown (ii) MOLECULE TYPE: peptide (ix) FEATURE:
(A) NAME/KEY: Modified-site
(B) LOCATION: 10
(D) OTHER INFORMATION: /note= "The Tyr residue at position 10
may be phosphorylated.

(xi) SEQUENCE DESCRIPTION: SEQ ID NO:26:

Asp Met Ser Lys Asp Glu Ser Val Asp Tyr Val Pro Met Leu Asp Met
1               5                   10                  15

Lys (2) INFORMATION FOR SEQ ID NO:27:

(i) SEQUENCE CHARACTERISTICS:
(A) LENGTH: 9 amino acids
(B) TYPE: amino acid
(D) TOPOLOGY: unknown (ii) MOLECULE TYPE: peptide (ix) FEATURE:
(A) NAME/KEY: Modified-site
(B) LOCATION: 5
(D) OTHER INFORMATION: /note= "The Tyr residue at position 5
may be phosphorylated.

(xi) SEQUENCE DESCRIPTION: SEQ ID NO:27:

Asp Asp Pro Ser Tyr Val Asn Val Gln
1               5

(2) INFORMATION FOR SEQ ID NO:28:

(i) SEQUENCE CHARACTERISTICS:
(A) LENGTH: 9 amino acids
(B) TYPE: amino acid
(D) TOPOLOGY: unknown (ii) MOLECULE TYPE: peptide (ix) FEATURE:
  (A) NAME/KEY: Modified-site
  (B) LOCATION: 5
  (D) OTHER INFORMATION: /note= "The Tyr residue at position 5 may be phosphorylated.

(xi) SEQUENCE DESCRIPTION: SEQ ID NO:28:

Val Asn Ala Thr Tyr Val Asn Val Lys
1               5

(2) INFORMATION FOR SEQ ID NO:29:

(i) SEQUENCE CHARACTERISTICS:
    (A) LENGTH: 4 amino acids
    (B) TYPE: amino acid
    (D) TOPOLOGY: unknown (ii) MOLECULE TYPE: peptide (xi) SEQUENCE DESCRIPTION: SEQ ID NO:29:

Tyr Val Xaa Val
1

(2) INFORMATION FOR SEQ ID NO:30:

(i) SEQUENCE CHARACTERISTICS:
    (A) LENGTH: 9 amino acids
    (B) TYPE: amino acid
    (D) TOPOLOGY: unknown (ii) MOLECULE TYPE: peptide (ix) FEATURE:
    (A) NAME/KEY: Modified-site
    (B) LOCATION: 5
    (D) OTHER INFORMATION: /note= "The Tyr residue at position 5 may be phosphorylated.

(xi) SEQUENCE DESCRIPTION: SEQ ID NO:30:

Ile Gly Glu His Tyr Val His Val Asn
1               5

(2) INFORMATION FOR SEQ ID NO:31:

(i) SEQUENCE CHARACTERISTICS:
    (A) LENGTH: 16 amino acids
    (B) TYPE: amino acid
    (D) TOPOLOGY: unknown (ii) MOLECULE TYPE: peptide (ix) FEATURE:
    (A) NAME/KEY: Modified-site
    (B) LOCATION: 5
    (D) OTHER INFORMATION: /note= "The Tyr residue at position 5 may be phosphorylated.

(ix) FEATURE:
    (A) NAME/KEY: Modified-site
    (B) LOCATION: 12
    (D) OTHER INFORMATION: /note= "The Tyr residue at position 31 may be phosphorylated.

(xi) SEQUENCE DESCRIPTION: SEQ ID NO:31:

Ile Gly Glu His Tyr Val His Val Asn Ala Thr Tyr Val Asn Val Lys
1               5                   10                  15

We claim:

1. A peptide having the sequence (SEQ ID NOS: 5 and 6)

$X_N$-YVN(or H)V-$X_C$ wherein $X_N$ and $X_C$ are each sequences of from 0 to 16 amino acids, said peptide being selected from the group consisting of H-Asp-Asp-Pro-Ser-Tyr*-Val-Asn-Val-Gln-OH
H-Val-Asn-Ala-Thr-Tyr*-Val-Asn-Val-Lys-OH
H-Ile-Gly-Glu-His-Tyr*-Val-His-Val-Asn-OH
H-Ile-Gly-Glu-His-Tyr*-Val-His-Val-Asn-Ala-Thr-Tyr*-Val-Asn-Val-Lys-OH
H-Tyr*-Val-His-Val-Asn-Ala-Thr-Tyr-OH
H-Tyr*-Val-His-Val-Asn-Ala-Thr-Tyr*-Val-Asn-Val-Lys-OH
H-Tyr*-Val-Asn-Val-Lys-Cys-Val-Ala-OH
(SEQ ID NOS: 27, 28, 30, 31, 20, 21, and 22, respectively) wherein Tyr* is a phosphorylated or unphosphorylated tyrosine residue.

2. A peptide according to claim 1 which is H-Asp-Asp-Pro-Ser-Tyr*-Val-Asn-Val-Gln-OH (SEQ. ID NO: 27) wherein Tyr* is a phosphorylated or unphosphorylated tyrosine residue.

3. A peptide according to claim 1 which is H-Val-Asn-Ala-Thr-Tyr*-Val-Asn-Val-Lys-OH (SEQ. ID NO: 28) wherein Tyr* is a phosphorylated or unphosphorylated tyrosine residue.

4. A peptide according to claim 1 which is H-Ile-Gly-Glu-His-Tyr*-Val-His-Val-Asn-OH (SEQ. ID NO: 30) wherein Tyr* is a phosphorylated or unphosphorylated tyrosine residue.

5. A peptide according to claim 1 which is H-Ile-Gly-Glu-His-Tyr*-Val-His-Val-Asn-Ala-Thr-Tyr*-Val-Asn-Val-Lys-OH (SEQ. ID NO: 31) wherein Tyr* is a phosphorylated or unphosphorylated tyrosine residue.

6. A peptide according to claim 1 which is H-Tyr*-Val-His-Val-Asn-Ala-Thr-Tyr*-OH (SEQ. ID NO: 20) wherein Tyr* is a phosphorylated or unphosphorylated tyrosine residue.

7. A peptide according to claim 1 which is H-Tyr*-Val-His-Val-Asn-Ala-Thr-Tyr*-Val-Asn-Val-Lys-OH (SEQ. ID NO: 21) wherein Tyr* is a phosphorylated or unphosphorylated tyrosine residue.

8. A peptide according to claim 1 which is H-Tyr*-Val-Asn-Val-Lys-Cys-Val-Ala-OH (SEQ. ID NO: 22) wherein Tyr* is a phosphorylated or unphosphorylated tyrosine residue.

9. A peptide of the formula

H—Tyr*—Asp—Ala—Arg—Val—His—Thr—Pro—OH
H—Tyr*—Arg—Ala—Thr—Phe—Pro—Glu—Asp—OH
H—Tyr*—Pro—Leu—Thr—Asp—Met—Ser—Pro—OH
H—Tyr*—His—Gly—Thr—Leu—Leu—Asp—Asn—OH
H—Tyr*—Met—Lys—His—Gly—Asp—Leu—Arg—OH
H—Tyr*—Leu—Ala—Ser—Lys—Lys—Phe—Val—OH
H—Tyr*—Asp—Lys—Glu—Tyr—Tyr—Ser—Val—OH
H—Tyr*—Tyr—Ser—Val—His—Asn—Lys—Thr—OH
H—Tyr*—Ser—Val—His—Asn—Lys—Thr—Gly—OH
H—Tyr*—Pro—Asp—Val—Asn—Thr—Phe—Asp—OH
H—Tyr*—Leu—Leu—Gln—Gly—Arg—Arg—Leu—OH
H—Tyr*—Cys—Pro—Asp—Pro—Leu—Tyr—Glu—OH
H—Tyr*—Glu—Val—Met—Leu—Lys—Cys—Trp—OH
H—Tyr*—Pro—Ser—Leu—Leu—Ser—Ser—Glu—OH (which correspond to SEQ. ID NOS: 7–19 and 23, respectively)

wherein Tyr* is a phosphorylated or unphosphorylated tyrosine residue.

10. The peptide as claimed in claim 2, wherein Tyr* is a phosphorylated tyrosine residue.

11. The peptide as claimed in claim 3, wherein Tyr* is a phosphorylated tyrosine residue.

12. The peptide as claimed in claim 4, wherein Tyr* is a phosphorylated tyrosine residue.

13. The peptide as claimed in claim 5, wherein Tyr* is a phosphorylated tyrosine residue.

14. The peptide as claimed in claim 6, wherein Tyr* is a phosphorylated tyrosine residue.

15. The peptide as claimed in claim 7, wherein Tyr* is a phosphorylated tyrosine residue.

16. The peptide as claimed in claim 8, wherein Tyr* is a phosphorylated tyrosine residue.

17. The peptide as claimed in claim 9, wherein Tyr* is a phosphorylated tyrosine residue.

* * * * *